United States Patent [19]
Arndt et al.

[11] 4,098,823
[45] Jul. 4, 1978

[54] MONOSPIROALKYL DERIVATIVES OF PROSTAGLANDINS

[75] Inventors: Henry Clifford Arndt; William Gerard Biddlecom; Warren Dexter Woessner, all of Madison, Wis.

[73] Assignee: Miles Laboratories, Inc., Elkhart, Ind.

[21] Appl. No.: 758,124

[22] Filed: Jan. 10, 1977

Related U.S. Application Data

[63] Continuation-in-part of Ser. No. 657,222, Feb. 11, 1976, abandoned.

[51] Int. Cl.$^2$ .............................................. C07C 49/46
[52] U.S. Cl. .............................. 260/586 G; 424/305; 424/331; 424/343; 560/118
[58] Field of Search ................................... 260/586 G

[56] References Cited

FOREIGN PATENT DOCUMENTS 7,558,036   5/1975   Japan .................................. 260/468

*Primary Examiner*—Gerald A. Schwartz
*Attorney, Agent, or Firm*—Richard W. Winchell

[57] ABSTRACT

Novel monospiroalkyl analogues or derivatives of prostaglandin A, E and F are useful modifiers of smooth muscle activity. The compounds have valuable pharmacalogical properties as platelet antiaggregating agents and gastric antisecretory agents. The compounds are also valuable pharmacological agents for increasing femoral blood flow and decreasing blood pressure and heart rate.

7 Claims, No Drawings

MONOSPIROALKYL DERIVATIVES OF PROSTAGLANDINS

CROSS REFERENCE TO RELATED APPLICATION

This application is a continuation-in-part of copending U.S. patent application Ser. No. 657,222, filed Feb. 11, 1976 now abandoned.

BACKGROUND OF THE INVENTION

Field of the Invention

Compounds of this invention are analogues of natural prostaglandins.

Natural prostaglandins are twenty-carbon atom alicyclic compounds related to prostanoic acid which has the following structure:

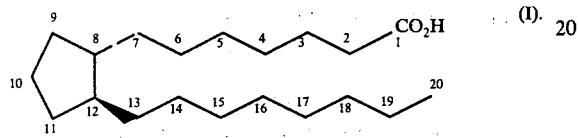

By convention, the carbon atoms of I are numbered sequentially from the carboxylic carbon atom. An important stereo-chemical feature of I is the trans-orientation of the side-chains $C_1$–$C_7$ and $C_{13}$–$C_{20}$. All natural prostaglandins have this orientation. In I, as elsewhere in this specification, a dashed line (---) indicates projection of a convalent bond below the plane of a reference carbon atom (alpha-configuration), while a wedged line (◂ represents direction above that plane (beta-configuration). Those conventions apply to all compounds subsequently discussed in this specification.

In one system of nomenclature suggested by N. A. Nelson (J. Med. Chem., 17: 911 (1974)), prostaglandins are named as derivatives or modifications of the natural prostaglandins. In a second system, the I.U.P.A.C. (International Union of Pure and Applied Chemistry) system of nomenclature, prostaglandins are named as substituted heptanoic acids. Yet a third system of nomenclature is frequently used by those skilled in the prostaglandin art. In this third system (also described by Nelson), all prostaglandins are named as derivatives or modifications of prostanoic acid (structure I) or prostane (the hydrocarbon equivalent of structure I). This system is used by Chemical Abstracts and may become an I.U.P.A.C. accepted system.

Natural prostaglandins have the structures,

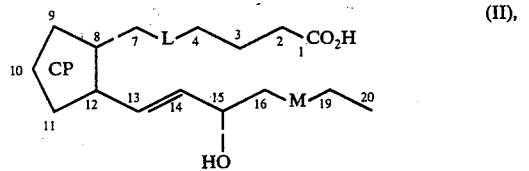

in which:

L and M may be ethylene or cis-vinylene radicals and the five-membered ring

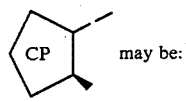 may be:

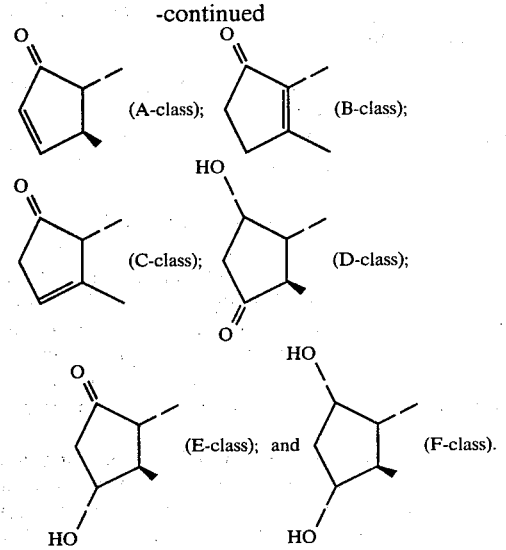

Prostaglandins are classified according to the functional groups present in the five-membered ring and the presence of double bonds in the ring or chains. Prostaglandins of the A-class (PGA or prostaglandin A) are characterized by an oxo group at $C_9$ and a double bond at $C_{10}$ $C_{11}$ ($\Delta^{10,11}$); those of the B-class (PGB) have an oxo group at $C_9$ and a double bond at $C_8$–$C_{12}$ ($\Delta^{8,12}$); compounds of the C-class (PGC) contain an oxo group at $C_9$ and a double bond at $C_{11}$–$C_{12}$ ($\Delta^{11,12}$); members of the D-class (PGD) have an oxo group at $C_{11}$ and an alpha-oriented hydroxy group at $C_9$; prostaglandins of the E-class (PGE) have an oxo group at $C_9$ and an alpha-oriented hydroxyl group at $C_{11}$; and members of the F-class (PGF) have an alpha-directed hydroxyl group at $C_9$ and an alpha-oriented hydroxyl group at $C_{11}$. Within each of the A, B, C, D, E, and F classes of prostaglandins are three subclassifications based upon the presence of double bond in the side-chains at $C_5$–$C_6$, $C_{13}$–$C_{14}$, or $C_{17}$–$C_{18}$. The presence of a trans-unsaturated bond only at $C_{13}$–$C_{14}$ is indicated by the subscript numeral 1; thus, for example, $PGE_1$ (or prostaglandin $E_1$) denotes a prostaglandin of the E-type (oxo group at $C_9$ and an alpha-hydroxyl at $C_{11}$) with a trans-double bond at $C_{13}$–$C_{14}$. The presence of both a trans-double bond at $C_{13}$–$C_{14}$ and a cis-double bond at $C_5$–$C_6$ is denoted by the subscript numeral 2; for example, $PGE_2$. Lastly, a trans-double bond at $C_{13}$–$C_{14}$, a cis-double bond at $C_5$–$C_6$ and a cis-double bond at $C_{17}$–$C_{18}$ is indicated by the subscript numeral 3; for example, $PGE_3$. The above notations apply to prostaglandins of the A, B, C, D, and F series as well, however, in the latter the alpha-orientation of the hydroxyl group at $C_9$ is indicated by the subscript Greek letter α after the numerical subscript.

The three systems of nomenclature as they apply to natural $PGF_{3\alpha}$ are shown below:

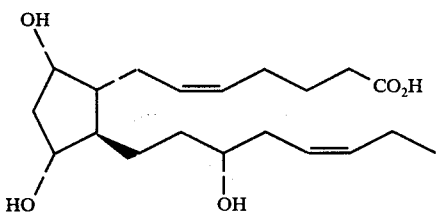

Nelson System:

Prostaglandin $F_{3\alpha}$ or $PGF_{3\alpha}$ (shortened form) I.U.P.A.C. System:

7-[3R, 5S-Dihydroxy-2R-(3S-hydroxyl-1E,5Z-octadienyl)cyclopent-1R-yl]-5-Z-heptenoic acid Third System (Chemical Abstracts):

(5Z, 9α, 11α, 13E, 15S, 17Z)-9,11,15-trihydroxyprosta-5,13,17-trien-1-oic acid.

It is important to note that in all natural prostaglandins there is an alpha-oriented hydroxyl group at $C_{15}$. In the Cahn-Ingold-Prelog system of defining stereochemistry, that $C_{15}$ hydroxyl group is in the S-configuration. The Cahn-Ingold-Prelog system is used to define stereochemistry of any asymmetric center outside of the carbocyclic ring in all three systems of nomenclature described above. This is in contrast to some prostaglandin literature in which the α,β designations are used, even at $C_{15}$.

11-Deoxy derivatives of PGE and PGF molecules do not occur as such in nature, but constitute a class of compounds which possess biological activity related to the parent compounds. Formula II represents 11-deoxy PGE and PGF compounds when:

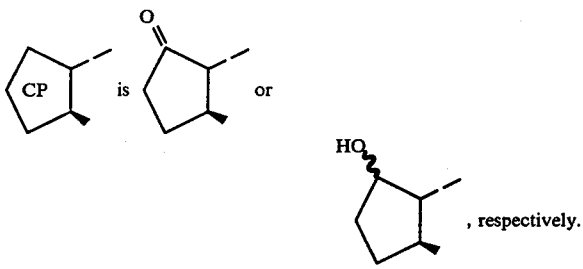

, respectively.

In this formula, and others of this patent specification a swung dash or serpentine line (∼) denotes a covalent bond which can be either in the alpha configuration (projecting below the plane of a reference carbon atom) or in the beta configuration (projecting above the plane of a reference carbon atom).

$PGF_\beta$ molecules also do not occur as such in nature, but constitute a class of compounds which possess biological activity related to the parent comounds. Formula II represents $PGF_\beta$ compounds when:

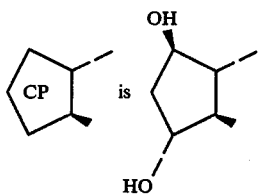

9-Deoxy derivatives of PGE do not occur as such in nature, but constitute a class of compounds which possess biological activity related to the parent compounds. Formula II represents 9-deoxy PGE compounds when:

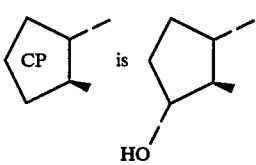

9-Deoxy-$\Delta^{9,10}$ derivaties of PGE do not occur as such in nature, but constitute a class of compounds which possess biological activity related to the parent compounds. Formula II represents 9-deoxy-$\Delta^{9,10}$ PGE compounds when:

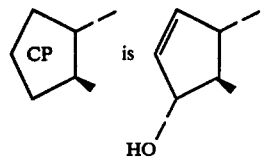

9a-Homo- and 9a-homo-11-deoxy-derivative of PGE and PGF molecules do not occur as such in nature, but constitute a class of compounds which possess biological activity related to the parent compounds. Formula II represents 9a-homo- and 9a-homo-11-deoxy-compounds of PGE and PGF when:

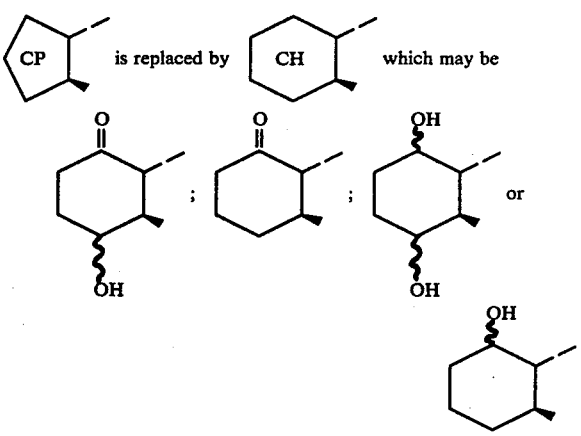

11a-Homo- derivatives of PGE, PGF and PGA molecules do not occur as such in nature, but constitute classes of compounds which are expected to posses biological activity related to the parent compounds. Formula II represents 11a-homo- derivatives of PGE, PGF and PGA molecules when:

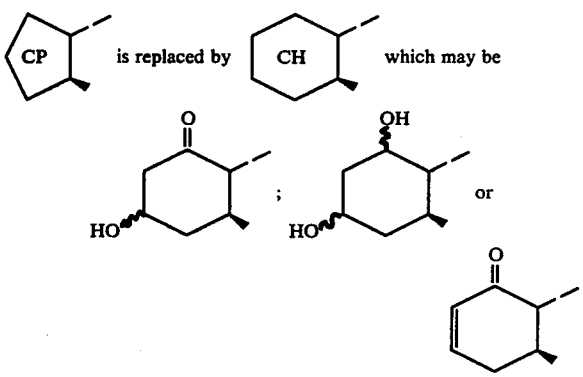

11-Epi-PGE and PGF molecules do not occur as such in nature, but constitute classes of compounds which possess biological activity related to the parent compounds. Formula II represents 11-epi-compounds of PGE and PGF when:

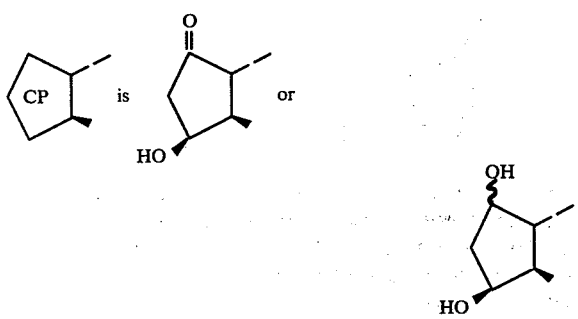

8Iso-, 12iso or 8,12-bis iso (ent) prostaglandins do not occur as such in nature, but constitute classes of compounds which possess biological activity related to the parent compounds. Formula II represents 8iso-, 12iso- or 8,12-bis iso (ent) compounds when:

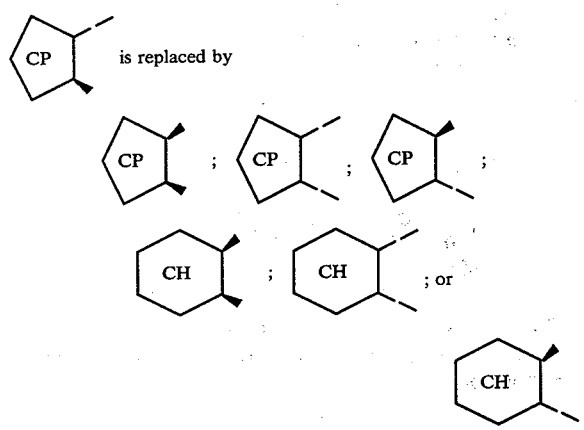

These iso modifications of Formula II may be divided into all of the sub-classes with varying ring oxygenation as described above.

Recent research indicates that prostaglandins are ubiquitous in animal tissues and that prostaglandins, as well as their synthetic anlogues, have important biochemical and physiological effects in mammalian endocrine, reproductive, central and peripheral nervous, sensory, gastro-intestinal, hematic, respiratory, cardiovascular, and renal systems.

In mammalian endocrine systems, experimental evidence indicates prostaglandins are involved in the control of hormone synthesis or release in hormone-secretory glands. In rats, for example $PGE_1$ and $PGE_2$ increase release of growth hormone with $PGA_1$ increased synthesis of that hormone. In sheep, $PGE_1$ and $PGF_{1\alpha}$ inhibit ovarian progesterone secretion. In a variety of mammals, $PGF_{1\alpha}$ and $PGF_{2\alpha}$ act as luteolytic factors. In mice, $PGE_1$, $PGE_2$, $PGF_{1\alpha}$ and $PGF_{1\beta}$ increase thyroid activity. In hypophysectomized rats, $PGE_1$, $PGE_2$ and $PGF_{1\alpha}$ stimulate steroidogenesis in the adrenal glands.

In the mammalian male reproductive system, $PGE_1$ contracts the smooth muscle of the vas deferens. In the female reproductive system, PGE and $PGF_\alpha$ compounds contract uterine smooth muscle. In general, PGE, PGB and PGA compounds relax in vitro human uterine muscle strips, while those of the $PGF_\alpha$ class contact such isolated preparations. PGE compounds in general promote fertility in the female reproductive system while $PGF_{2\alpha}$ has contragestational effects. $PGF_{2\alpha}$ also appears to be involved in the mechanism of menstruation. In general, $PGE_2$ exerts potent oxytocic effects in inducing labor, while $PGF_{2\alpha}$ induces spontaneous abortions in early pregnancy.

$PGF_\alpha$ and PGE compounds have been isolated from a variety of nervous tissue and they seem to act as neurotransmitters. $PGE_1$ retards whereas $PGF_{2\alpha}$ facilitates transmission in motor pathways in the central nervous system. It has been reported that $PGE_1$ and $PGE_2$ inhibit transmitter release from adrenergic nerve endings in the guinea pig.

Prostaglandins stimulate contraction of gastrointestinal smooth muscle in vivo and in vitro. In dogs, $PGA_1$, $PGE_1$ and $PGE_2$ inhibit gastric secretion. $PGA_1$ exhibits similar activity in man.

In most mammalian respiratory tracts, compounds of the PGE and PGF class relax in vitro preparations of tracheal smooth muscle. In that preparation, $PGE_1$ and $PGE_2$ relax while $PGF_{2\alpha}$ contracts the smooth muscle. PGE and PGF compounds are normally found in the human lung, and it is postulated that some cases of bronchial asthma involve an imbalance in the production or metabolism of those compounds.

Prostaglandins are involved in certain hematic mechanisms in mammals. $PGE_1$, for example, inhibits thrombogenesis in vitro through its effects on blood platelets.

In a variety of mammalian cardiovascular systems, compounds of the PGE and PGA class are vasodilators whereas those of the $PGF_\alpha$ class are vasoconstrictors, by virtue of their action on vascular smooth muscle.

Prostaglandins are naturally found in the kidney and reverse experimental and clinical renoprival hypertension.

The clinical implications of prostaglandins and their analogues are far-ranging and include, but are not limited to the following: in obstetrics and gynecology, they may be useful in fertility control, treatment of menstrual disorders, induction of labor, and correction of hormone disorders; in gastroenterology, they may be useful in the treatment of peptic ulcers and various disorders involving motility, secretion, and absorption in the gastrointestinal tract; in the respiratory area, they may be beneficial in therapy of bronchial asthma and other diseases involving bronchoconstriction; in hematology, they may have utility as anti-clotting agents in diseases such as venous thrombosis, thrombotic coronary occlusion and other diseases involving thrombi; in circulatory diseases they have therapeutic utility in hypertension, peripheral vasopathies, and cardiac disorders.

For a more complete review of chemical, physiological and pharmacological aspects of the prostaglandin, consult the following references: The prostaglandins, Vol. I., P. Ramwell, Ed., New York, Plenum Press, 1973; Ann, N.Y. Acad. Sci., 180: 1-568 (1971): and Higgins and Braunwald, J. Am. Med. Assn., 53: 92-112 (1972).

DESCRIPTION OF THE PRIOR ART

Great Britain patent application No. 027,844 filed June 14, 1971 discloses cycloalkyl or adamantyl derivatives of prostaglandins.

Netherland Pat. No. 7,315,307 discloses cycloalkyl, adamantyl or 2-norbornyl derivatives of prostaglandins.

Japan Pat. No. 75 58,036 discloses 16-butylprostadienoic acids.

U.S. Pat. No. 3,867,375 discloses a process and reagents for preparing prostaglandins and derivatives.

SUMMARY

Novel and useful monospiroalkyl analogues of prostaglandins having the following structural formula III constitute the subject matter of this invention:

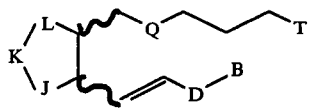
(III)

In formula III:

D is R-hydroxymethylene or S-hydroxymethylene radical;

J is a methylene, R-hydroxymethylene, S-hydroxymethylene or a methine radical such that J is methine only when K is methine;

K is a methylene, ethylene or a methine radical such that K is ethylene only when J is methylene and K is methine only when J is methine;

L is a carbonyl, R-hydroxymethylene or S-hydroxymethylene radical;

Q is an ethylene or Z-vinylene radical;

T is an alkoxycarbonyl having from 1 to 3 carbon atoms inclusive in the alkyl chain, carboxyl, or hydroxymethyl radical or pharmacologically acceptable non-toxic carboxy salts; and B is a monospiroalkyl radical of the formula

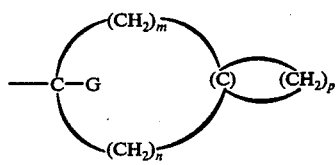

where $m$ is an integer having a value of from 0 to 2; $n$ is an integer having a value of from 1 to 4; $p$ is an integer having a value of from 3 to 11; and the sum of the integers $m$ and $n$ is less than or equal to 4 and where G is hydrogen or lower alkyl of 1 to 3 carbon atoms.

The numbering system and the stereochemistry nomenclature used for the prostaglandins of this invention are according to the I.U.P.A.C. definitive and tentative rules which designate the carboxylic acid side chain as the parent compound. In Formula III, a swung dash or serpentive line ($\sim$) denotes a covalent bond which can be either in the alpha configuration (projecting below the plane of a reference carbon atom) or in the beta configuration (projecting above the plane of a reference carbon atom). As used herein, cis or trans isomerism around double bonds respectively in designated by affixes Z (zusammen) and E (entgegen). Chirality around asymmetric carbon atoms is designated by affixes R (rectus) and S (sinister).

Analogues or derivatives of the A-, E-, and F- classes of the natural prostaglandins are represented by Formula III. Thus when, L is carbonyl, and both J and K are methine radicals, III represents analoges of the A-class of prostaglandins:

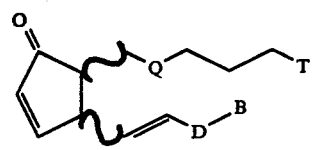
(IIIa)

When L is carbonyl, K is methylene or ethylene and J is methylene or hydroxymethylene such that K is ethylene only when J is methylene, III represents analogues of the E-class, 11-deoxy-E- class or 9a-homo-11-deoxy-E-class of prostaglandins:

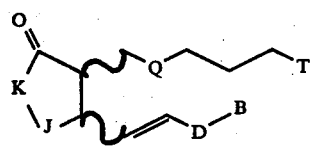
(IIIb)

When L is carbonyl, K is methylene and J is R-hydroxymethylene or S-hydroxymethylene, III represents analogues of the E-class of prostaglandins:

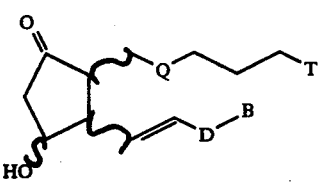
(IIIc)

When L is carbonyl and both J and K are methylene, III represents analogues of the 11-deoxy-E-class of prostaglandin:

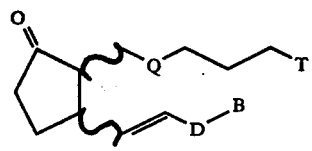
(IIId)

When L is carbonyl, K is ethylene and J is methylene, III represents analogues of 9a-homo-11-deoxy-PGE class of prostaglandins.

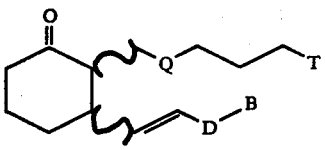
(IIIe)

When L is R-hydroxymethylene or S-hydroxymethylene; K is methylene or ethylene, such that K is ethylene only when J is methylene, J is R-hydroxymethylene, S-hydroxymethylene or methylene, III represents analogue of $PGF_\alpha$, $PGF_\beta$, 11-deoxy-$F_\alpha$, 11-deoxy-$F_\beta$, 9a-homo-11-deoxy $F_\alpha$ and 9a-homo-11-deoxy $F_\beta$:

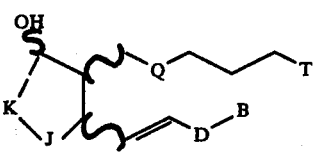
(IIIf)

When L is R-hydroxymethylene or S-hydroxymethylene; K is methylene; and J is R-hydroxymethylene or S-hydroxymethylene, III represents analogues of PGF$_\alpha$ and PGF$_\beta$

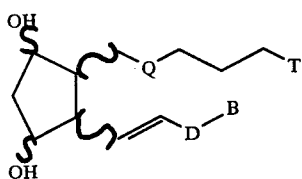

When L is formula IIIf above is S-hydroxymethylene and J is R-hydroxymethylene, analogues of the F$_\alpha$ class of prostaglandins are represented.

When L in formula IIIf above is R-hydroxymethyl and J is R-hydroxymethylene, analogues of the F$_\beta$ class of prostaglandins are represented.

When J is formula IIIf above is methylene, analogues of the 11-deoxy-F$_\alpha$ and 11-deoxy-F$_\beta$ are represented.

When in formula IIIf above, K is ethylene and J is methylene, then analogues of the 9a-homo-11-deoxy F$_\alpha$ and 9a-homo-11-deoxy F$_\beta$ classes of prostaglandin are represented.

When Q, in formulae IIIa, IIIb, IIIc, IIId, IIIe, IIIf and IIIg above is ethylene, then analogues of the A$_1$, E$_1$, 11-deoxy-E$_1$, 9a-homo-11-deoxy-E$_1$, F$_{1\alpha}$, F$_{1\beta}$, 11-deoxy-F$_{1\alpha}$, 11-deoxy-F$_{1\beta}$, 9a-homo-11-deoxy-F$_{1\alpha}$ and 9a-homo-11-deoxy-F$_{1\beta}$ classes of prostaglandins are respectively represented.

When Q in formulae IIIa, IIIb, IIIc, IIId, IIIe, IIIf and IIIg above is Z-vinylene, then analogues of the A$_2$, E$_2$, 11-deoxy-E$_2$, 9a-homo-11-deoxy-E$_2$, F$_{2\alpha}$, F$_{2\beta}$, 11-deoxy-F$_{2\alpha}$, 11-deoxy-F$_{2\beta}$, 9a-homo-11-deoxy-F$_{2\alpha}$ and 9a-homo-11-deoxy-F$_{2\beta}$ classes of prostaglandins are respectively represented.

When T in formulae IIIa, IIIb, IIIc, IIId, IIIe, IIIf and IIIg above is an alkoxycarbonyl having from 1 to 3 carbon atoms inclusive in the alkyl chain, carboxyl, or pharmacologically acceptable nontoxic carboxy salts, then the C$_1$ esters, acids and salts of the various A-, E- and F- classes of prostaglandins are represented.

When T in formulae IIIa, IIIb, IIIc, IIId, IIIe, IIIf and IIIg above is hydroxymethyl, then the C$_1$ alcohols of the various A-, E- and F- classes of prosgaglandins are represented.

When formula III above is

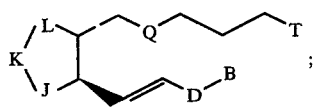

then III represents the natural configuration of prostaglandins about the C$_8$ and C$_{12}$ positions, and when formula III is

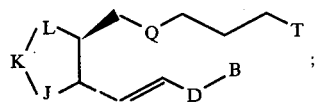

then III represents the 8, 12-bis iso (ent) class of prostaglandins.

The term (dl) as used herein refers to racemic mixtures and where used as a prefix to a particular isomer structure, it designates a racemic mixture of the indicated isomer and its mirror image.

Useful intermediates in the preparation of compounds of formula III are represented by the formula:

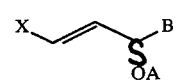

wherein:
X is an iodo or bromo radical;
A is an acid-labile hydroxyl-protecting group selected from the class consisting of 1-ethoxyethyl, trimethylsilyl, tert-butyl-dimethylsilyl, 2-ethoxyprop-2-yl, tetrahydropyran-2-yl, or triphenylmethyl radicals; and
B is selected from the class of monospiroalkyl radicals of the formula

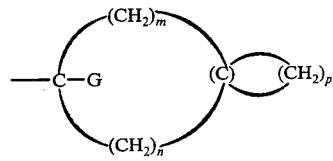

where $m$ is an integer having a value of from 0 to 2; $n$ is an integer having a value of from 1 to 4; $p$ is an integer having a value of from 3 to 11; and the sum of the integers $m$ and $n$ is less than or equal to 4 and where G is hydrogen or lower alkyl of 1 to 3 carbon atoms.

DESCRIPTION OF THE INVENTION

Compounds having Formula III are prepared via the 1,4-conjugate addition of organocopper reagents to cyclopentenones as reported by Sih, et al., (J. Amer. Chem. Soc., 97: 857,865 (1975) and references cited therein). The novel compounds of Formula III are prepared according to the reaction sequence depicted in Table A.

TABLE A

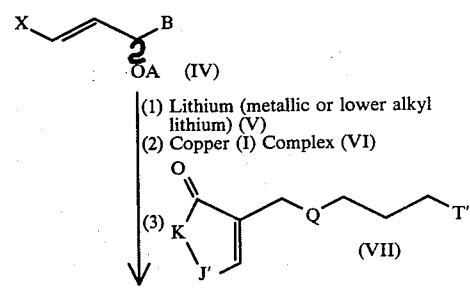

TABLE A-continued

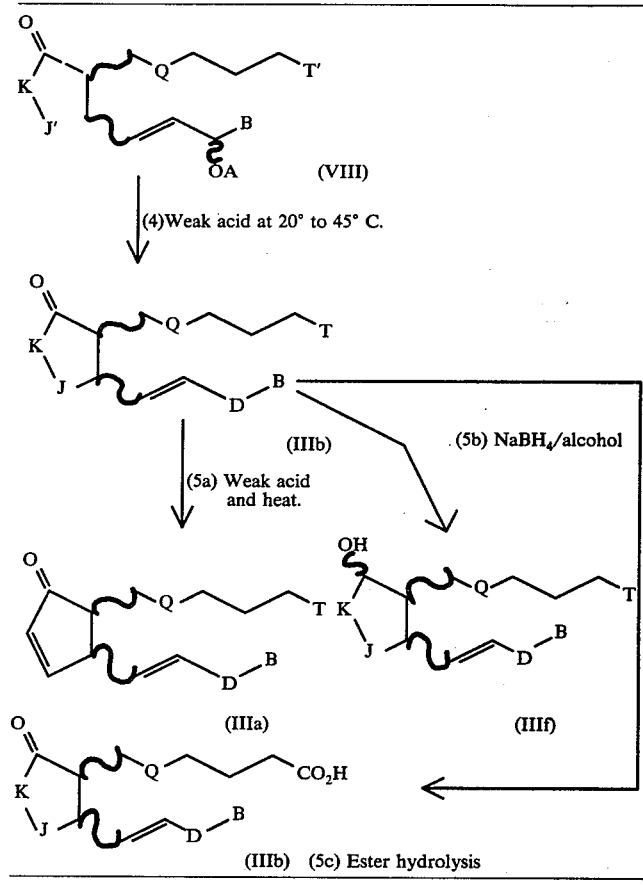

In Table A, Compound IV, where X is an iodo or bromo radical and A is an acid-labile hydroxyl-protecting group, is contacted and reacted with Metallic lithium or lower alkyl lithium (Compound V) at from about −80° C to 0° C for about 0.25 to 3.0 hours in an inert solvent, such as ether, tetrahydrofuran, hexane, pentane, toluene, mixtures thereof and the like, under an inert atmosphere, such as argon, nitrogen and the like. Copper(I) complex (Compound VI) is added, usually as a solution in an inert solvent, to the reaction mixture and the mixture is then stirred at less than about −20° C for about 0.25 to 1.0 hour. A solution of Compound VII, where J' is methylene or =CHOA and T' is alkoxycarbonyl or —CH$_2$OA, usually in an inert solvent, is added to the reaction mixture which is then allowed to warm to about −20° C to 25° C over a 0.5 to 5 hour period to yield the intermediate Compound VIII after quenching with a proton donor. Treatment of the latter compound under hydrolysis conditions such as with a weakly-acidic water mixture, such as acetic acid-water (65:35 V/V) with 10% tetrahydrofuran, under an inert atmosphere at a temperature of about 20° C to 45° C for about 0.5 to 48 hours cleaves the acid-labile hydroxyl-protecting groups (described in J. Amer. Chem. Soc., 94:6194[1972]) to yield Compound IIIb.

Where J and K of Compound IIIb are respectively hydroxymethylene and methylene, dehydration of Compound IIIb with a weakly-acidic water mixture, such as acetic acid-water, at about 60° C to 80° C (described in J. Org. Chem., 34:3552 [1969]) yields Compound IIIa. Compound IIIa is also obtained as a by-product of the acidic hydrolysis of Compound VIII.

Reduction of Compound IIIB with sodium borohydride in an alcoholic or other suitable polar solvent (described in J. Org. Chem., 34:3552[1969]) yields Compound IIIf.

When T of Compound IIIb (where J is methylene) or IIIf is alkoxycarbonyl, cleavage of the ester group with a base, such as sodium hydroxide or potassium hydroxide in a mixed organic solvent such as water-tetrahydrofuran, water-p-dioxane or water-alcohol (described in J. Amer. Chem. Soc., 94:7823 [1973]) yields the corresponding acid, i.e. where T is carboxyl. Where J and T of Compound IIIb are respectively hydroxymethylene and alkoxycarbonyl, cleavage of the ester group by exposure to Rhizopus oryzae (described in J. Amer. Chem. Soc. 95:1676[1973] or with a suitable esterase or lipase (described in U.S. Pat. No. 3,769,166 and German patent application No. 2,242,792) yields the corresponding acid, i.e. where T is carboxyl.

Treatment of Compounds IIIa or IIIb, where T is carboxyl or alkoxycarbonyl group, with a carbonyl protecting group followed by reduction and treatment with nitrous acid yields the corresponding primary alcohol, i.e. where T is hydroxymethyl (described in U.S. Pat. No. 3,636,120). Suitable carbonyl protecting groups include lower alkoxyamines, semicarbazide or thiosemicarbazides. Suitable reducing agents include lithium aluminum hydride, lithium borohydride, and diisobutyl aluminum hydride.

Non-toxic, pharmacologically acceptable salts of Compound III can be prepared by neutralization of III, where T is carboxyl, with an equivalent or an excess amount of the corresponding non-toxic salt-forming organic or inorganic base. The salts are prepared by procedures which are well-known in the art. Suitable salts include sodium, potassium, ammonium and the like. The salts may be isolated by lyophilization of the resulting mixture, or by filtration if sufficiently unsoluble, or by similar well-known techniques.

All compounds of this invention can be isolated from reaction mixtures and purified by well-known organic chemistry procedures. For example, the compounds can be isolated by dilution of the reaction mixture with water; extraction with a water-immiscible solvent, such as benzene, cyclohexane, ether, ethyl acetate, methylene chloride, toluene and the like; chromatography; distillation and the like or a combination of these procedures. Purfication of these compounds can be accomplished by methods which are well-known in the art for the purification of prostaglandins, lipids, fatty acids, and fatty esters. For example, such methods as reverse phase partition chromatography; countercurrent distribution; adsorption chromatography on acid washed magnesium silicate, neutral or acid washed silica gel, alumina or silicic acid; preparative paper chromatography; preparative thin layer chromatography; high pressure liquid-liquid chromatography; gas-liquid chromatography and the like or combinations thereof can be used to purify the compounds produced by the processes of this invention.

The starting reactants used in the above procedures are well-known or easily prepared by known methods. For instance, in the reaction sequence depicted in Table A, Compound V, i.e. metallic lithium or lower alkyl lithium such as t-butyllithium, sec-butyllithium or n-butyllithium are commercially available or prepared by well-known organic chemistry methods. Examples of Compound VI, i.e. copper(I) complexes, include: [hexamethylphosphorous triamide]$_2$ copper(I)pentyne (preparation described in J. Amer. Chem. Soc., 94:7210[1972]; and J. Org. Chem., 31:4071[1966]); tri-n-butylphosphine-copper(I)iodide (preparation described in Inorg. Synth., 7:9[1963]); hexamethylphosphorus triamide-copper(I)iodide (preparation described in Prostaglandins, 7:387[1974]); copper(I) thiophenolate (preparation described in Synthesis 662[1974]) and the like. Examples of Compound VII which are employed in the synthesis of III include: Methyl 7-(5-oxocyclopent-1-enyl)heptanoate (preparation described in Tet. Let., 24:2435[1972]); methyl 7-[3R-(tetrahydropyran-2-yloxy)-5-oxocyclopent-1-enyl]heptanoate (preparation described in J. Amer. Chem. Soc., 95:1676[1973]); 1-(tetrahydropyran-2-yloxy)-7-(5-oxocyclopent-1-enyl)-heptane (preparation described in Tet. Let., 773[1972]); Methyl 7-(5-oxocyclopent-1-enyl)hept-5Z-enoate (preparation described in J. Org. Chem., 38: 3413[1973]); Methyl 7-[3R-(tetrahydropyran-2-yloxy)-5-oxocyclopent-1-enyl]hept-5Z-enoate (preparation described in Tet. Let., 2313[1973]); Methyl 7-(6-oxocyclohex-1-enyl)hept-5Z-enoate (preparation described in copending U.S. Ser. No. 657,221, filed Feb. 11, 1976; 1-(tetrahydropyran-2-yloxy)-7-[3R-tetrahydropyran-2-yloxy)-5-oxocyclopent-1-en-1R-yl]heptane (preparation described in copending U.S. Ser. No. 657,221, filed Feb. 11, 1976); and 1-(tetrahydropyran-2-yloxy)-7-[3R-(tetrahydropyran-2-yloxy)-5-oxocyclopent-1-enyl]hept-5Z-ene (preparation described in copending U.S. Ser. No. 651,221, filed Feb. 11, 1976, which is incorporated herein by reference.

Compound IV of Table A is prepared according to the reaction sequence depicted in Table B. Examples of compounds having formula IV which are used in the reaction IV → III include: 1-iodo-3RS-(1-ethoxyethoxy)-3-(spiro-[3.3]hept-2-yl)-1E-propene; 1-iodo-3RS-(1-ethoxyethoxy)-3-(spiro[5.5]undec-3-yl)-1E-propene and the like. The synthesis of Compound IV from the corresponding spiroalkyl acid IVa can be accomplished via the reaction sequence of Table B by well-known organic chemistry procedures.

TABLE B

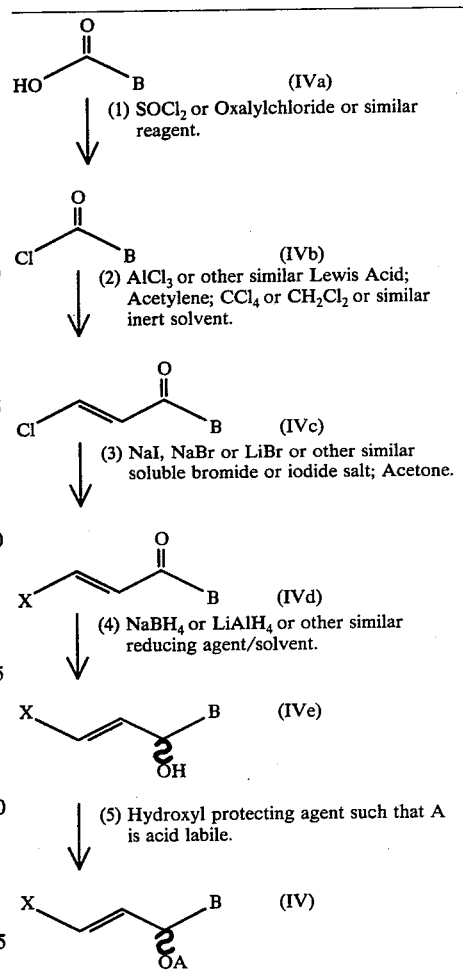

In IVa → IVb, the monospiroalkyl acid IVa is converted to the acid chloride IVb using an acid chloride forming reagent such as thionyl chloride, oxalyl chloride, phosphorus trichloride and the like as described in Fieser & Fieser, Reagents For Organic Synthesis, I:1158, J. Wiley & Sons Inc. (1967). In IVb → IVc, the acid chloride IVb is reacted with acetylene in an inert solvent, such as carbon tetrachloride, methylene chloride or the like, in the presence of a Lewis acid such as aluminum chloride, stannic chloride or the like to produce the β-chlorovinyl ketone IVc as described in Chem. Revs., 161(1965) and Org. Synth., IV:186, J. Wiley & Sons Inc. (1963). In IVc → IVd, the β-chlorovinyl ketone IVc is converted into the corresponding β-iodo-or β-bromo-vinyl ketone IVd, where X is an iodo or bromo radical, using a soluble salt, such as sodium iodide, sodium bromide, lithium bromide or the like, in a polar inert solvent, such as acetone, acetonitrile and the like, as described in J. Amer. Chem. Soc., 94: 7210(1972). In IVd → IVe, Compound IVd is reduced to the corresponding β-iodo- or β-bromo-vinyl alcohol using a suitable reducing agent, such as sodium borohydride in alcohol solvent or lithium aluminum hydride in ether solvent as described in J. Amer. Chem. Soc., 94:7210(1972). In IVe → IV, Compound IVe is contacted and reacted with a suitable acid-labile hydroxyl-protecting group (A) such as dihydropyran as ethylvinyl ether in the presence of an acid catalyst such as p-toluenesulfonic acid, 98% sulfuric acid or phosphorus oxychloride; or a trialkylsilylchloride, such as trimethylsilylchloride or t-butyldimethylsilylchloride, or triphenymethylbromide in the presence of a basic catalyst such as triethylamine or imidazole. Any protecting group which is removable under mildly acid conditions and is stable to alkyllithium and alkylcopper(I)reagents can also be suitably used, see J. Org. Chem. 37:1947(1972).

In Table B, compound IVc can be prepared from compound IVa, where B is

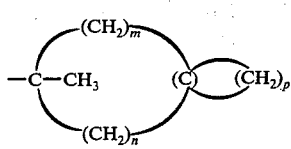

by reacting IVa with methyl lithium in an inert solvent such as ethyl ether to produce the sprioalkyl methyl ketone as described in Org. Reactions, 18:1(1970). The spiroalkyl methyl ketone is then dissolved in ethyl ether and methyl formate and treated with sodium hydride to form the spiroalkyl hydroxyvinyl ketone as described in J. Amer. Chem. Soc. 76:552 (1954). The hydroxyvinyl ketone is then treated with an acid chloride forming reagent such as thionyl chloride to form the β-chlorovinyl ketone IVc as described in Chem. Revs., 161(1965).

Examples of the corresponding monospiroalkyl compounds having formula IVa include: spiro[3.3]heptyl-2-carboxylic acid: spiro[5.5] undecyl-3-carboxylic acid and 2-methylspiro [3.3]heptyl-2-carboxylic acid. The compounds of formula IVa are either commercially available or easily prepared by well-known techniques from commercially available materials. For example, the compound 1,1-cyclobutanedicarboxylic acid (Beil. 9:725; available from Aldrich Chemical Co., Inc.) is reduced with lithium aluminum hydride to produce 1,1-di(hydroxymethyl)cyclobutane by a similar procedure as described in Fieser & Fieser, Reagents for Org. Synth., 1:581, J. Wiley & Sons, (1967). This compound is then esterified with p-toluenesulfonyl chloride to produce 1,1-di(toluenesulfonylmethyl)cyclobutane. This latter compound is cyclized with diethyl malonate to produce spiro[3.3]heptane-2,2-dicarboethoxy ester followed by hydrolysis in ethanolic potassium hydroxide to produce spiro[3.3]heptyl-2,2-dicarboxylic acid. This compound is then thermally decarboxylated to produce spiro[3.3]heptyl-2-carboxylic acid which is used in the reaction sequence depicted in Table B to produce 1-iodo-3RS-(1-ethoxyethoxy)-3-(spiro[3.3]hept-2-yl)-1E-propene. These procedures are described collectively in J. Org. Chem., 29:2914(1964); J. Org. Chem., 31:4069 (1966); and Justus Liebigs Ann. Chem., 685:74(1965).

Spiro[5.5]undecyl-3-carboxylic acid (either commercially available or prepared by well-known methods such as described in U.S. Pat. No. 3,350,442) is used in the reaction sequence depicted in Table B to produce 1-iodo-3RS-(1-ethoxyethoxy)-3-(spiro[5.5]undec-3-yl)-1E-propene.

The compound 2-methylspiro[3.3]heptane-2-carboxylic acid can be prepared from the spiro[3.3]heptane-2-carboxylic acid as described in Tet. Let, 2221 (1974) and J. Org. Chem., 35:262 (1970).

The compounds represented by Formula III inhibit aggregation of human platelets in vitro as demonstrated in the following Example 15. It is that feature which distinguishes the compounds of this invention over the natural prostaglandins. Of the natural prostaglandins, only $PGE_1$ displays a similar activity. Preferred compounds of those represented by formula III which inhibit aggregation of platelets are compounds TR-4120 and TR-4845. It should be noted that while the natural $PGE_1$ compounds display a similar activity, the compounds of the present invention do not exhibit the undesirable side effects observed in the natural $PGE_1$ compounds.

The prostaglandin analogues of this invention also stimulate in vitro and in vivo smooth muscle preparations derived from a variety of tissues and organs of experimental animals. Such smooth muscle assays are widely utilized to determine the activity of natural prostaglandins as well as prostaglandin analogues (Bundy et al., Ann. N.Y. Acad. Sci., 180:76[1961]; Bergstrom et al., Pharmacol. Revs., 20:1[1968]). Details of the activity of certain compounds having Formula III are presented in Example 15 below.

Compounds of the formulae, collectively referred to as IIIx,

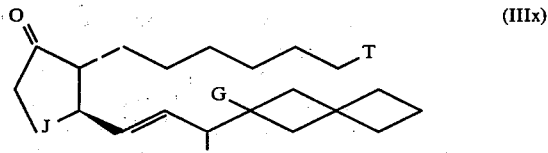

(IIIx)

or

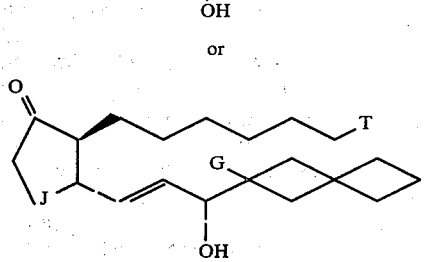

wherein J is R-hydroxymethylene or methylene; T is an alkoxycarbonyl having from 1 to 3 carbon atoms inclusive in the alkyl chain, carboxyl, hydroxymethyl or pharmacologically acceptable nontoxic carboxy salts; and G is hydrogen or methyl, are useful in a therapeutic method of inhibiting gastric secretion in an individual for whom such therapy is indicated by administering to that individual an amount of a compound having structure IIIx that is effective in inhibiting or decreasing gastric secretion. The term "individual" as utilized in this specification means a human being or a standard experimental animal that is a model for a human being. Indications for use of compounds IIIx are any conditions in which inhibition or decrease of gastric secretion is desirable, such as peptic or duodenal ulcers, hyperacidity, and the like. The term "effective antisecretory amount" or any equivalent of the term means a dose or a series of doses that will decrease or inhibit gastric secretion. Although that amount will vary from individual to individual and from indication to indication, it is easily determined by one skilled in the art without undue experimentation. Compounds IIIx may be administered by known conventional modes of therapeutic administration such as intravenous, parenteral, buccal, rectal or oral. The oral mode, however, is preferred. Dose forms for administration of compounds IIIx can be prepared by recognized methods in the pharmaceutical sciences. Use of methyl 7-{3R-hydroxy-5-oxo-2R-[3R-hydroxy-3-(spiro[3.3]hept-2-yl)-1E-propenyl]cyclopent-1R-yl}heptanoate; 7-{3R-hydroxy-5-oxo-2R-[3R-hydroxy-3-(spiro[3.3]hept-2-yl)-1E-propenyl]cyclopent-1R-yl}heptan-1-ol; methyl 7-{3R-hydroxy-5-oxo-2R-[3R-hydroxy-3-(2-methylspiro[3.3]hept-2-yl)-1E-propenyl]cyclopent-1R-yl}heptanoate; 7-{3R-hydroxy-5-oxo-2R-[3R-hydroxy-3-(2-methylspiro[3.3]hept-2-yl)-1E-propenyl]cyclopent-1R-yl}heptan-1-ol; and dl 7-{5-oxo-2R-[3R-hydroxy-3-(spiro[3.3]hept-2-yl)-1E-propenyl]cyclopent-1R-yl}heptanoic acid are preferred.

The preferred compounds TR-4120 and TR-4845 mentioned above are represented by the formula IIIy

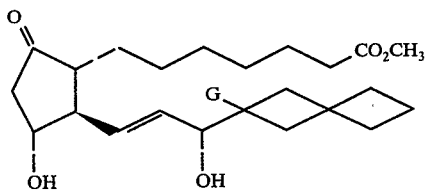

IIIy where G is hydrogen or methyl, and are particularly useful in a therapeutic method of inhibiting platelet aggregation in an individual for whom such therapy is indicated by administering to that individual an amount of compound IIIy that is effective in inhibiting or decreasing platelet aggregation. Indications for use of compound IIIy are any condition in which inhibition or decrease of platelet aggregation is desirable, such as ischemic heart disease, high blood pressure, post surgical conditions and the like. The term "effective antiaggregating amount" or any equivalent of the term means a dose or a series of doses that will decrease or inhibit platelet aggregates. Although that amount will vary from individual to individual and from indication to indication, it is easily determined by one skilled in the art without undue experimentation. Compounds IIIy may be administered by known conventional modes of therapeutic administration such as intravenous, rectal, oral and the like. Dose forms for administration of compounds IIIy can be prepared by recognized methods in the pharmaceutical science.

The compound, 7-{3R-hydroxy-5-oxo-2R-[3R-hydroxy-3-(2-methylspiro[3.3]hept-2-yl)-1E-propenyl]cyclopent-1R-yl}heptan-1-ol (TR-4852), which is represented by the formula

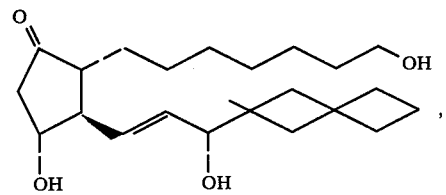

is particularly useful in a therapeutic method for inducing uterine contractions in an individual for whom such therapy is indicated by administering to that individual an amount of Compound TR-4852 above that is effective in inducing uterine contractions. Indications for use of Compound TR-4852 are any condition in which inducement of uterine contraction is desirable, such as inducement of labor. The term "effective uterine contracting amount" or any equivalent of the term means a dose or a series of doses that will induce uterine contraction. Although that amount will vary from individual to individual and from indication to indication, it is easily determined by one skilled in the art without undue experimentation. Compound TR-4852 may be administered by known conventional modes of therapeutic administration such as intravenous, rectal, oral and the like. Dose forms for administration of Compound TR-4852 can be prepared by recognized methods in the pharmaceutical science.

The following Table C illustrates preferred embodiments of the present invention compiled by Compound No., Example No. and identified by the I.U.P.A.C. system of nomenclature.

TABLE C

| Compound No. | Example No. | I.U.P.A.C. Nomenclature | Chemical Abstracts Nomenclature |
| --- | --- | --- | --- |
| TR-4126 | 2A | Methyl 7-{5-oxo-2R-[3S-hydroxy-3-(spiro[3.3]hept-2-yl)-1E-propenyl]-cyclopent-3-en-1R-yl}heptanoate. | Methyl 15S-Hydroxy-16,18-methano-18,20-methano-9-oxoprosta-10, 13E-dien-1-oate |
| TR-4127 | 2B | Methyl 7-{5-oxo-2R-[3R-hydroxy-3-(spiro[3.3]hept-2-yl)-1E-propenyl]-cyclopent-3-en-1R-yl}hepanoate. | Methyl 15R-hydroxy-16, 18-methano-18, 20-methano-9-oxoprosta-10, 13E-dien-1-oate |
| TR-4120 | 1A | Methyl 7-{3R-hydroxy-5-oxo-2R-[3R-hydroxy-3-(spiro[3.3]hept-2-yl)-1E-propenyl]cyclopent-1R-yl}heptanoate. | Methyl 11α, 15R-Dihydroxy-16, 18-methano-18, 20-methano-9-oxoprost-13E-en-1-oate |
| TR-4121 | 1B | Methyl 7-{3R-hydroxy-5-oxo-2R-[3S-hydroxy-3-(spiro[3.3]hept-2-yl)-1E-propenyl]cyclopent-1R-yl}heptanoate. | Methyl 11α, 15S-dihydroxy-16, 18-methano-18, 20-methano-9-oxoprost-13E-en-1-oate |
| TR-4713 | 7A | 7-{3R-hydroxy-5-oxo-2R-[3R-hydroxy-3-(spiro[3.3]hept-2-yl)-1E-propenyl]-cyclopent-1R-yl}heptan-1-ol. | 16, 18-Methano-18, 20-methano-1, 11α, 15R-trihydroxyprost-13E-en-9-one |
| TR-4714 | 7B | 7-{3R-hydroxy-5-oxo-2R-[3S-hydroxy-3-(spiro[3.3]hept-2-yl)-1E-propenyl]-cyclopent-1R-yl}heptan-1-ol. | 16, 18-Methano-18, 20-methano-1, 11α, 15S-trihydroxyprost-13E-en-9-one |
| TR-4020 | 5A | dl 7-{5-oxo-2R-[3R-hydroxy-3-(spiro[5.5]undecan-3-yl)-1E-propenyl]cyclopent-1R-yl}heptanoic acid. | (±) 15R-Hydroxy-16, 19-ethano-19, 20-butano-9-oxoprost-13E-en-1-oic acid |
| TR-4021 | 5B | dl 7-{5-oxo-2R-[3S-hydroxy-3-(spiro[5.5]undecan-3-yl)-1E-propenyl]cyclopent-1R-yl}heptanoic acid. | (±) 15S-Hydroxy-16, 19-ethano-19, 20-butano-9-oxoprost-13E-en-1-oic acid |
| TR-4136 | 4A | dl 7-{5-oxo-2R-[3S-hydroxy-3-(spiro[3.3]hept-2-yl)-1E-propenyl]-cyclopent-1R-yl}heptanoic acid. | (±) 15S-Hydroxy-16, 18-methano-18, 20-methano-9-oxoprost-13E-en-1-oic acid |

TABLE C-continued

| Compound No. | Example No. | I.U.P.A.C. Nomenclature | Chemical Abstracts Nomenclature |
|---|---|---|---|
| TR-4137 | 4B | dl 7-{5-oxo-2R-[3R-hydroxy-3-(spiro[3.3]hept-2-yl)-1E-propenyl]-cyclopent-1R-yl}heptanoic acid. | (±) 15R-Hydroxy-16, 18-methano-18, 20-methano-9-oxoprost-13E-en-1-oic acid |
| TR-4146 | 6A | dl 7-{5-oxo-2R-[3S-hydroxy-3-(spiro[3.3]hept-2-yl)-1E-propenyl]-cyclopent-1R-yl}hept-5Z-enoic acid. | (±) 15S-Hydroxy-16, 18-methano-18, 20-methano-9-oxoprosta-5Z, 13E-dien-1-oic |
| TR-4147 | 6B | dl 7-{5-oxo-2R-[3R-hydroxy-3-(spiro[3.3]hept-2-yl)-1E-propenyl]-cyclopent-1R-yl}hept-5Z-enoic acid. | (±) 15R-Hydroxy-16, 18-methano-18, 20-methano-9-oxoprosta-5Z, 13E-dien-1-oic |
| TR-4139 | 3A | Methyl 7-{3R,5S-dihydroxy-2R-[3S-hydroxy-3-(spiro[3.3]hept-2-yl)-1E-propenyl]cyclopent-1R-yl}heptanoate. | Methyl 16, 18-methano-18, 20-methano-9α, 11α, 15S-trihydroxyprost-13E-en-1-oate |
| TR-4138 | 3B | Methyl 7-{3R, 5R-dihydroxy-2R-[3S-hydroxy-3-(spirol[3.3]hept-2-yl)-1E-propenyl]cyclopent-1R-yl}heptanoate. | Methyl 16, 18-methano-18, 20-methano-9β, 11α, 15S-trihydroxyprost-13E-en-1-oate |
| TR-4726 | 8A | Ethyl 7-{3R-hydroxy-5-oxo-2R-[3R-hydroxy-3-(spiro[3.3]hept-2-yl)-1E-propenyl]cyclopent-1R-yl}hept-5Z-enoate. | Ethyl 11α, 15R-dihydroxy-16, 18-methano-18, 20-methano-9-oxoprosta-5Z, 13E-dien-1-oate |
| TR-4727 | 8B | Ethyl 7-{3R-hydroxy-5-oxo-2R-[3S-hydroxy-3-(spiro[3.3]hept-2-yl)-1E-propenyl]cyclopent-1R-yl}hept-5Z-enoate. | Ethyl 11α, 15S-dihydroxy-16, 18-methano-18, 20-methano-9-oxoprosta-5Z- 13E-dier-1-oate |
| 4841 | 12A | 7-{3R-hydroxy-5-oxo-2R-[3S-hydroxy-3-(2-methylspiro[3.3]hept-2-yl)-1E-propenyl]cyclopent-1R-yl}heptan-1-ol | 16-Methyl-16,18-methano-18,20-methano-1,11α,15S-trihydroxyprost-13E-en-9-one |
| TR-4852 | 12B | 7-{3R-hydroxy-5-oxo-2R-[3R-hydroxy-3-(2-methylspiro[3.3]hept-2-yl)-1E-propenyl]cyclopent-1R-yl}heptan-1-ol | 16-Methyl-16,18-methano-18,20-methano-1,11α,15R-trihydroxyprost-13E-en-9-one |
| 4842 | 13A | Methyl 7-{3R-hydroxy-5-oxo-2R-[3S-hydroxy-3-(2-methylspiro[3.3]hept-2-yl)-1E-propenyl]cyclopent-1R-yl} heptanoate | Methyl 11α,15S-dihydroxy-16-methyl-16,18-methano-18,20-methano-9-oxoprost-13E-en-1-oate |
| 4845 | 13B | Methyl 7-{3R-hydroxy-5-oxo-2R-[3R-hydroxy-3-(2-methylspiro[3.3]hept-2-yl)-1E-propenyl]cyclopent-1R-yl} heptanoate | Methyl 11α,15R-dihydroxy-16-methyl-16,18-methano-18,20-methano-9-oxoprost-13E-en-1-oate |
| TR-4758 | 11B | dl Methyl-7-{6-ozo-2R-δ3S-hydroxy-3-(spiro[3.3]hept-2-yl)-1E-propenyl]cyclohex-1R-yl}hept-5Z-enoate | dl Methyl-15S-hydroxy-9-oxo-9a-homo-16,18-methano-18,20-methanoprost-5Z, 13E-dien-1-oate |
| TR-4759 | 11A | dl Methyl-7-{6-oxo-2R-[3R-hydroxy-3-(spiro[3.3]hept-2-yl)-1E-propenyl]cyclohex-1R-yl}hept-5Z-enoate | dl Methyl-15R-hydroxy-9-oxo-9a-homo-16,18-methano-18,20-methanoprost-5Z, 13E-dien-1-oate |

In order to further illustrate the novel aspects of the present invention, the following examples are presented. It should be recognized that these examples are provided by way of illustration only and are not intended to limit in any way the invention disclosed herein. Compounds identified by compound number in the following examples refer to the compounds compiled in Table C.

EXAMPLE 1

This example illustrates a typical preparation of Prostaglandin $E_1$ Analogues.

Compounds TR 4120 and TR 4121 were prepared according to the procedure which follows. A mixture containing 2.62 grams (0.0059 moles) of 1-iodo-3RS-(1-ethoxyethoxy)-3-(spiro-[3.3]hept-2-yl)-1E-propene (see Example 9 for preparation) and 24 ml. of dry ether (distilled from benzophenone ketyl) was prepared and cooled to −78° C. with stirring under an argon atmosphere. Then 6.95 ml of 1.7 M t-butyllithium (0.0118 mole) in n-pentane was added and the mixture was stirred at a temperature of −78° C for 2 hours. A solution of 0.766 grams of Copper(I)pentyne (0.0059 moles) and 1.66 ml of hexamethyl phosphorus triamide in 8 ml of dry ether was added to the reaction flask with stirring at −78° C. The resulting mixture was stirred 30 minutes at −78° C and 1.74 grams (0.0536 mole) of methyl 7[3R-(tetrahydropyran-2-yloxy)-5-oxocyclopent-1-enyl]heptanoate in 4.0 ml of dry ether was added thereto. The mixture was stirred for 30 minutes at −78° C and subsequently brought to −20° C and stirred for 1.5 hours. The mixture was quenched by the addition of 115 ml of 20% (v/v) aqueous ammonium sulfate and extracted with 50 ml of ether. The aqueous material was extracted with 100 ml (2×50 ml) of ether. The ether extracts were combined and washed with 50 ml of 2% (v/v) sulfuric acid. The aqueous material was back-extracted with 100 ml (2×50 ml) of ether. The combined ether extracts were filtered through diatomaceous earth (Celite), washed with 50 ml of saturated sodium bicarbonate solution and subsequently washed with 50 ml of saturated sodium chloride solution. The washed ether extract was then dried over anhydrous magnesium sulfate, filtered through diatomaceous earth (Celite) and the solvent removed in vacuo. The residue was stirred with 12 ml of acetic acid-water-tetrahydrofuran (65:35:10 v/v) at 22° C for 15 hours. The solvents were removed in vacuo and the residue was taken up in 50 ml of water. The water mixture was extracted with 150 ml (3×50 ml) of ether-ethyl acetate (1:1 v/v). The organic mixture was washed with 50 ml of saturated sodium bicarbonate solution and then washed with 50 ml of saturated sodium chloride solution. The washed organic mixture was then dried over anhydrous magnesium sulfate, filtered through diatomaceous earth (Celite) and the solvents was removed in vacuo. The residue was chromatographed by column chromatography using an 85:15 (w/w) silicic acid: diatomaceous earth (Celite) support and using a benzene-ethyl acetate gradient elution to yield 168.4 mg of Compound TR 4120 and 162.8 mg of Compound TR 4121.

A. Compound TR 4120 had the following spectral properties:

Analysis — IR: $\nu_{max}^{CHCl_3}$: 3600–3300 cm$^{-1}$, 2950 cm$^{-1}$, 1740 cm$^{-1}$ and 1710 cm$^{-1}$.

NMR(CDCl$_3$): δ1.1–2.9, multiplet, 27H; δ3.65, singlet, 3H; δ3.6–4.2, multiplet, 3H; δ4.6, multiplet, 1H; δ5.6 ppm, multiplet, 2H;

$[\alpha]_D$ (CDCl$_3$, c. 0.87): −61.1°.

B. Compound TR 4121 had the following spectral properties:

Analysis — IR: $\nu_{max}^{CHCl_3}$: 3600–3300 cm$^{-1}$, 2950 cm$^{-1}$, 1740 cm$^{-1}$ and 1710 cm$^{-1}$.

NMR(CDCl$_3$): δ1.0–2.9, multiplet, 27H; δ3.6, singlet, 3H; δ3.6–4.1, multiplet, 3H; δ4.6, multiplet, 1H; δ4.5 ppm, multiplet, 2H.

$[\alpha]_D$ (CHCl$_3$, c. 1.0): −56.5°.

EXAMPLE 2

This Example illustrates the preparation of Prostaglandin A analogues.

A mixture, containing 0.1234 grams (0.315 m mole) of Compounds TR 4120 and TR 4121, prepared as described in Example 1, and 3.5 ml of glacial acetic acid and 0.7 ml of water was heated at 60° C for 24 hours. The solvents were removed in vacuo and the residue was taken up in 20 ml of water and 20 ml of ether-ethyl acetate (1:1 v/v). The ether-ethyl acetate extract was washed with 20 ml of saturated sodium bicarbonate solution and then washed with 20 ml saturated sodium chloride solution. The washed extract was dried over anhydrous magnesium sulfate and filtered. The solvents were removed from the extract in vacuo. The residue was chromatographed by column chromatography using a silicic acid-diatomaceous earth (85:15 w/w) support and using a benzene-ethyl acetate gradient to yield 15.9 mg of compound TR 4126 and 27.6 mg of Compound TR 4127.

A. Compound TR 4126 had the following spectral properties:

Analysis — IR: $\nu_{max}^{CHCl_3}$: 2940 cm$^{-1}$, 1730 cm$^{-1}$, and 1705 cm$^{-1}$.

NMR(CDCl$_3$): δ0.9–2.5, multiplet, 25H; δ3.3, multiplet, 1H; δ3.7, singlet, 3H; δ3.8–4.0, multiplet, 2H; δ5.5, multiplet, 2H; δ6.1, multiplet, 1H; δ7.25 ppm, multiplet, 1H.

$[\alpha]_D$ (CHCl$_3$, c. 0.96): + 83.5°.

B. Compound TR 4127 had the following spectral properties:

Analysis — IR: $\nu_{max}^{CHCl_3}$: 2930 cm$^{-1}$, 1730 cm$^{-1}$, and 1710 cm$^{-1}$.

NMR(CDCl$_3$): δ1.1–2.4, multiplet, 25H; δ3.2, multiplet, 1H; δ3.63, singlet, 3H; δ3.7–4.1, multiplet, 2H; δ5.5, multiplet, 2H; δ6.1, multiplet, 1H; δ7.4 ppm, multiplet, 1H.

$[\alpha]_D$ (CHCl$_3$, c. 0.92); + 77°.

EXAMPLE 3

This Example illustrates the preparation of Prostaglandin $F_{1\alpha}$ and $F_{1\beta}$ analogues.

About 10 ml of anhydrous methanol was mixed with 0.11 grams (0.28 mmol) of Compound TR 4120 prepared in the manner described in Example 1. The mixture was cooled in an ice-methanol bath and a mixture of 0.0635 grams (0.168 mmol) of sodium borohydride partially dissolved in 15 ml of anhydrous methanol was added. The mixture was stirred for 30 minutes at −20° C then brought to room temperature and stirred for an additional 2.5 hours. The solvents were removed in vacuo. The residue was taken up in 30 ml of water and extracted with 120 ml (4×30 ml) of ether-ethyl acetate (1:1 v/v). The ether-ethyl acetate extract were combined and washed with 30 ml of saturated sodium chloride solution. The washed extract was dried over anhydrous magnesium sulfate and filtered and the solvents were then removed in vacuo. The residue was chromatographed by column chromatograply using silicic acid: diatomaceous earth (Celite) 85:15 (w/w) support and using a benzene-ethyl acetate gradient elution to yield 32.2 mg of TR 4139 and 28.2 mg of TR 4138.

A. Compound TR 4139 had the following spectral properties

Analysis — IR: $\nu_{max}^{CHCl_3}$: 3600–3100 cm$^{-1}$, 2950 cm$^{-1}$, and 1700 cm$^{-1}$.

NMR(CDCl$_3$): δ1.1–2.6, multiplet, 27H; δ3.6–4.2, multiplet, 5H; δ5.5, multiplet, 1H; δ5.45 ppm, multiplet, 2H.

$[\alpha]_D$ (CHCl$_3$ c. 1.26): +32.2°.

B. Compound TR 4138 had the following spectral properties:

Analysis — IR: $\nu_{max}^{CHCl_3}$: 3600–3100 cm$^{-1}$, 2950 cm$^{-1}$, and 1730 cm$^{-1}$.

NMR(CDCl$_3$): δ1.1–2.6, multiplet, 27H; δ3.7, singlet, 3H; δ3.7–4.1, multiplet, 5H; δ5.5 ppm, multiplet, 2H.

$[\alpha]_D$ (CHCl$_3$, c. 1.41): +6.8°.

EXAMPLE 4

Preparation of Compounds TR 4136 and TR 4137

A mixture containing 1.31 grams, (0.00295 mole) of 1-iodo-3RS-(1-ethoxyethoxy)-3-(spiro[3.3]hept-2-yl)-1E-propene (see Example 9 for preparation of this compound) and 12 ml of dry ether (distilled from benzophenone ketyl, b.p. 34° C) was prepared and cooled to −78° C with stirring under an argon atmosphere. Then 3.475 ml (0.0059 mole) of a solution (1.7M) of t-butyllithium in pentane was added. The resultant mixture was stirred for 2 hr at −78° C. Copper(I) pentyne (0.383 g, 0.00295 mole) and 0.83 ml of dry hexamethylphosphorus triamide in 4 ml of dry ether was added to the reaction flask. The resulting reaction mixture was stirred for 30 minutes at −78° C and 0.6 grams (0.00268 mole) of methyl 7-(5-oxocyclopent-1-enyl)heptanoate in 2 ml of dry ether was added thereto. The mixture was stirred for 30 minutes at −78° C and subsequently brought to −20° C and stirred for 90 minutes. The mixture was quenched with 80 ml of 20% (w/v) aqueous ammonium sulfate solution. The mixture was shaken for 10 minutes with 30 ml of ether. The aqueous material was extracted with 150 ml (2×75 ml) of ether. The ether extracts were combined and washed with 30 ml of cold 2% (v/v) aqueous sulfuric acid. The aqueous material was back-extracted with 100 ml (2×50 ml) of ether. The combined ether extracts were filtered through diatomaceous earth (Celite), washed with 75 ml of saturated sodium bicarbonate solution and subsequently with 75 ml of saturated sodium chloride solution. The washed extract was then dried over anhydrous magnesium sulfate, and filtered through diatomaceous earth (Celite) the solvents were removed from the extract in vacuo. The residue was stirred with 25 ml of acetic acid-water-tetrahydrofuran (65:30:10 v/v/) at about 22° C for 1 hour. The solvents were removed in vacuo and the residue was taken up in 30 ml of water and 30 ml of ether-ethyl acetate (1:1 v/v). The aqueous material was extracted with 70 ml (2×35 ml) of ether-ethyl acetate (1:1 v/v). The ether-ethyl acetate extracts were combined and washed with 50 ml of saturated sodium bicarbonate solution and then washed with 50 ml of saturated sodium chloride solution. The washed ether-ethyl acetate extracts were dried over anhydrous magnesium sulfate and filtered through diatomaceous earth (Celite). The solvents were removed from the extract in vacuo. The residue was stirred with 25 ml of 5% (w/v) potassium hydroxide-methanol-water (1:1 v/v) for 2.5 hours. The methanol was removed in vacuo. The residual material was taken up in 50 ml of water and extracted with 90 ml (3×30 ml) of ethyl acetate. The organic material was backextracted with 50 ml (2×25 ml) of water. The aqueous material was acidified with 10% (w/v) aqueous hydrochloric acid and the products were extracted with 150 ml (3×50 ml) of ether. The ether extracts were combined and washed with 50 ml of saturated sodium chloride. The washed extract was dried over anhydrous magnesium sulfate and filtered through diatomaceous earth. The solvents were removed from the extract in vacuo. The residue was chromatographed by column chromatography using a silicic acid-diatomaceous earth (85:15 w/w) support and using a benzene-ethyl acetate elution gradient to yield 45.7 mg of Compound TR 4136 and 52.7 mg of Compound TR 4137.

A. Compound TR 4136 had the following spectral properties:

Analysis — IR: $\nu_{max}^{CHCl_3}$: 2940 cm$^{-1}$, 1730 cm$^{-1}$ and 1710 cm$^{-1}$.

NMR(CDCl$_3$): $\delta$1.0–2.9, multiplet, 29H; 3.95, multiplet, 1H; 5.5, multiplet, 2H; 7.75 ppm, broad singlet, 2H.

B. Compound TR 4137 had the following spectral properties:

Analysis — IR: $\nu_{max}^{CHCl_3}$: 3600 cm$^{-1}$, 2940 cm$^{-1}$, 1730 cm$^{-1}$, and 1710 cm$^{-1}$.

NMR(CDCl$_3$): $\delta$1.1–2.7, multiplet, 29H; 3.9, multiplet, 1H; 5.5, multiplet, 2H; 6.95 ppm, broad singlet, 2H.

EXAMPLE 5

Preparation of Compounds TR 4020 and TR 4021

Repeating in a similar manner the procedure of Example 4, but replacing 1-iodo-3RS-(1-ethoxyethoxy)-3-(spiro-[3.3]hept-2-yl)-1E-propene with 1-iodo-3RS-(1-ethoxyethoxy)-3-(spiro[5.5]undec-3-yl)-1E-propene (see Example 10 for preparation) yields the following 11-deoxy Prostaglandin E$_1$ analogues:

A. Compound TR 4020 had the following spectral properties:

Analysis — IR: $\nu_{max}^{CHCl_3}$: 3600–2400 cm$^{-1}$, 2950 cm$^{-1}$, 1740 cm$^{-1}$, and 1720 cm$^{-1}$.

NMR(CDCl$_3$): $\delta$0.7–2.6, multiplet, 37H; $\delta$3.9, multiplet, 1H; $\delta$5.6, multiplet, 2H; $\delta$6.1 ppm, multiplet, 2H.

B. Compound TR 4021 had the following spectral properties:

Analysis — IR: $\nu_{max}^{CHCl_3}$: 3500–2400 cm$^{-1}$, 1730 cm$^{-1}$, and 1710 cm$^{-1}$.

NMR(CDCl$_3$): $\delta$0.7–2.6, multiplet, 37H; $\delta$3.95, multiplet, 1H; $\delta$5.7, multiplet, 2H; $\delta$6.01 ppm, multiplet, 2H.

EXAMPLE 6

Preparation of Compounds TR 4146 and TR 4147

Repeating in a similar manner the procedure of Example 4, but replacing methyl 7-(5-oxocyclopent-1-enyl)heptanoate with methyl 7-(5-oxocyclopent-1-enyl)hept-5Z-enoate yields the following 11-desoxy Prostaglandin E$_2$ analogues.

A. Compound TR 4146 had the following spectral properties:

Analysis — IR: $\nu_{max}^{CHCl_3}$: 2950 cm$^{-1}$, 1730 cm$^{-1}$, and 1710 cm$^{-1}$.

NMR(CDCl$_3$): $\delta$1.8–3.0, multiplet, 25H; $\delta$4.0, multiplet, 1H; $\delta$5.45, multiplet, 4H; $\delta$7.2 ppm, broad singlet, 2H.

B. Compound TR 4147 had the following spectral properties:

Analysis — IR: $\nu_{max}^{CHCl_3}$2950 cm$^{-1}$, 1740 cm$^{-1}$ and 1715 cm$^{-1}$.

NMR(CDCl$_3$): $\delta$0.8–3.0, multiplet, 25H; $\delta$3.9 multiplet, 1H; $\delta$5.45, multiplet, 4H; $\delta$6.9 ppm, broad singlet, 2H.

EXAMPLE 7

Preparation of compounds TR 4713 and TR 4714

A solution of 606 mg (2.0 mmol) of 1-iodo-3RS-(1-ethoxyethoxy)-3-(spiro[3.3]hept-2-yl)-1E-propene in 11.0 ml of dry ether was stirred under argon at $-78°$, and 3.6 ml of 1.18M t-butyllithium in pentane was injected. The reaction mixture was stirred for 2.5 hr at $-78°$, then was transferred into a stirred, $-78°$ solution of 250 mg of copper(I) pentyne in 6.2 ml of dry ether (solubilized at 25° with 0.74 ml of hexamethylphosphorous triamide). The resultant complex was stirred for 0.5 hr at $-78°$, then a solution of 685 mg of 1-tetrahydropyran-2-yloxy-7-{3R-(tetrahydropyran-2-yloxy)-5-oxocyclopent-1-enyl}heptane in 3.7 ml of ether was injected dropwise over 10 min. The reaction mixture was stirred for 0.5 hr at $-78°$, and 1.5 hr at $-10°$. The reaction was quenched by the addition of 20% aqueous ammonium sulfate and the mixture extracted with ether. The ether extracts were combined and washed with 2% aqueous sulfuric acid, saturated aqueous sodium bicarbonate and brine, then dried (MgSO$_4$), filtered and solvent removed in vacuo to yield an orange oil. The oil was stirred with 54 ml of 65:35:10 acetic acid-water-THF for 18 hr at 25°. The solvents were removed by evaporation in vacuo and water added to the residue. The mixture was extracted with ether. The ether extracts were washed with saturated aqueous sodium bicarbonate and brine, then dried (MgSO$_4$), filtered and ether evaporated in vacuo to afford 629 mg of crude products as a yellow oil. The products were purified by column chromatography to afford 82.8 mg of Compound TR 4714; and 103 mg of Compound TR 4713

A. Compound TR 4713 had the following spectral properties:

Analysis — IR: $\lambda_{max}^{CHCl_3}$: 2.78, 2.95(broad), 5.75, 10.40$\mu$.

NMR(CDCl$_3$): 5.66, multiplet, 2, C$\underline{H}$=C$\underline{H}$ 3.2–4.3, multiplet, 7H, C$\underline{H}$OH $[\alpha]_D$ (CHCl$_3$, c. 0.94): $-57.9°$ Ms (70eV) 346(p-H$_2$O); 328(p-2H$_2$O).

B. Compound TR 4714 had the following spectral properties:

Analysis — IR: $\lambda_{max}^{CHCl_3}$ 2.78, 5.75, 10.40$\mu$

NMR(CDCl$_3$): $\delta$5.74, multiplet, 2H, trans-C$\underline{H}$=C$\underline{H}$) 3.2–4.7, multiplet, 7H, C$\underline{H}$O$\underline{H}$ $[\alpha]_D$ (CHCl$_3$, c. 1.0): $-53.5°$ Ms(70eV) 346(p-H$_2$O); 328(p-2H$_2$O).

EXAMPLE 8

Preparation of Compounds TR 4726 and TR 4727

Repeating in a similar manner the procedure of Example 1, but replacing methyl 7-[3R-(tetrahydropyran-2-yloxy)-5-oxocyclopent-1-enyl]heptanoate with ethyl 7-[3R-tetrahydropyran-2-yloxy)-5-oxocyclopent-1-enyl]hept-5Z-enoate yields the prostaglandin E$_2$ analogues TR 4726 and TR 4727.

A. Compound TR 4726 had the following spectral properties:

Analysis — IR: $\nu_{max}^{CHCl_3}$: 910, 970, 1075, 1160, 1740, 2840, 2950, 3400(broad), and 3600 cm$^{-1}$.

NMR(CDCl$_3$): $\delta$1.24, t, 3H, J=7HZ; 1.4 to 3,0, m, 23H; 3.3 to 4.3, m, 6H; 5.2 to 5.7, m, 4H.

Ms (70eV): m/e 386 (p-H$_2$O); 368 (p-2H$_2$O); 341 (p-H$_2$O—OC$_2$H$_5$); 309 (p-C$_7$H$_{11}$); 291 (p-C$_7$H$_{11}$—H$_2$O).
[α]$_D$(CHCl$_3$, c 0.95): −53.1°.

B. Compound TR 4727 had the following spectral properties:

Analysis — NMR,IR,Ms are essentially the same as for the compound 4726 above. [α]$_D$(CHCl$_3$, c 0.95): −60.0°.

EXAMPLE 9

This Example illustrates the preparation of the intermediate compound 1-iodo-3RS-(1-ethoxyethoxy)-3-(spiro[3.3]hept-2-yl)-1E-propene using the following procedure.

A. Preparation of 1,1-di(Hydroxymethyl)cyclobutane

Lithium aluminum hydride (63.4 g, 1.67 mole) was slurried in 600 ml of dry ether (distilled from benzophenone ketyl, bp 34° C). The slurry was cooled in an ice-water bath and a mixture of 100 g (0.69 mole) of 1,1-cyclobutanedicarboxylic acid (commercially available from Aldrich Chemical Co., Inc.) and 250 ml of dry ether was slowly added. The mixture was stirred at reflux for 1 hr, cooled and the excess hydride was destroyed by ethyl acetate addition. The mixture was treated with 1 liter of 6N hydrochloric acid and the products were extracted with 2 liters (4×500 ml) of ether. The organic material was washed with 250 ml of saturated sodium bicarbonate solution and 250 ml of saturated sodium chloride solution. It was dried over anhydrous magnesium sulfate, filtered and evaporated in vacuo to yield 49 g of pure 1,1-di(hydroxymethyl)cyclobutane.

Analysis — NMR(CDCl$_3$): δ1.85, multiplet, 6H; δ3.3–3.8 ppm, multiplet, 4H.

B. Preparation of 1,1-di(Toluenesulfonyloxymethyl)cyclobutane 1,1-di(Hydroxymethyl)cyclobutane (1.16 g, 0.01 mole) was mixed with 10 ml of dry pyridine (distilled from calcium hydride). The mixture was cooled to approximately 0° C and 5.0 g (0.0263 mole) of p-toluenesulfonyl chloride was added portion wise. The mixture was stirred for 3 hrs at 0° C then poured into 70 ml of cold 6N hydrochloric acid. Crude ditosylate was isolated by filtration. The crude material was recrystallized from methanol to yield 2.76 g (64.7%) of 1,1-di(toluenesulfonyloxymethyl)cyclobutane.

Analysis: NMR(CDCl$_3$): δ1.8, broad singlet, 6H; δ2.45, singlet, 6H; δ3.95, singlet, 4H; δ7.5, AB pattern, J=8HZ, 8H.

C. Preparation of Spiro[3.3]heptane-2,2-dicarboethoxy ester

Sodium metal (0.5 g, 0.022 mole) was dispersed in 10 ml of dry xylene (distilled from sodium hydride) by rapid stirring at 110° C. Diethyl malonate (6 g, 0.0375 mole, 5.67 ml) was added and the mixture was heated at 100° C until the sodium was consumed. 1,1-di(-toluenesulfonyloxymethyl)-cyclobutane (4 g, 0.009425 mole) was added and the mixture was heated at 157° C for 18 hr with stirring. The mixture was cooled and 20 ml of water was added. The phases were separated and the aqueous material was extracted with 150 ml (2×75 ml) of xylene. The organic material was washed with 50 ml of 6N hydrochloric acid and 50 ml of saturated sodium sulfate solution. It was dried over anhydrous magnesium sulfate, filtered and evaporated in vacuo. The residue was distilled at reduced pressure to yield 0.99 g (44%) of spiro[3.3]heptane-2,2-dicarboethoxy ester.

Analysis — bp: 98°–98.5° C/0.35 mm.

NMR(CDCl$_3$): δ1.25, triplet, 6H,J=7HZ; δ1.5–2.2, multiplet, 6H; δ2.48, multiplet, 4H; 4.2 ppm, quartet, 4H,J=7HZ.

D. Preparation of Spiro[3.3]heptane-2,2-dicarboxylic acid

Spiro[3.3]heptane-2,2-dicarboethoxy ester (14.4 g, 0.6 mole) was mixed with 13.45 g (0.24 mole) of potassium hydroxide and 114 ml of ethanol. The mixture was refluxed for 1 hr, cooled and then filtered. The cake was washed with 80 ml of absolute ethanol. The residue was dissolved in 50 ml of water and acidified with 60 ml of 50% aqueous sulfuric acid. The mixture was cooled and filtered to yield 10.4 g of spiro[3.3]heptane-2,2-dicarboxylic acid.

Analysis — NMR(CDCl$_3$): δ1.3–2.2, multiplet, 6H; 2.5, multiplet, 4H; 8.0–9.0 ppm, broad singlet, 2H.

E. Preparation of Spiro[3.3]heptane-2-carboxylic acid

Crude spiro[3.3]heptane-3,3-dicarboxylic acid (8.3 g, 0.046 mole) was thermally decarboxylated by heating the material at 220° C for 30 min. Heating was discontinued when the evolution of carbon dioxide ceased. The mixture was cooled to yield 5.38 g of spiro[3.3]heptane-2-carboxylic acid.

Analysis — NMR(CDCl$_3$): δ1.5–2.3, multiplet, 11H; 11.0 ppm, broad singlet, 1H.

F. Preparation of Spiro[3.3]heptane-2-carboxylic acid chloride

Spiro[3.3]heptane-3-carboxylic acid (8.5 g, 0.06 mole) was mixed with 14.5 g (0.124 mole, 9.2 ml) of thionyl chloride. The mixture was allowed to stir overnight at room temperature. The excess thionyl chloride was removed by distillation at atmospheric pressure. Spiro[3.3]heptane-2-carboxylic acid chloride (8.3 g, 86.4%) was isolated by distillation at reduced pressure.

Analysis — NMR(CDCl$_3$): δ1.8–2.6, multiplet, 10H; 3.45 ppm, multiplet, 1H.

G. Preparation of 1-Chloro-3(spiro[3.3]hept-2-yl)-1E-propen-3-one

A 100 ml 3-neck round bottom flask was fitted with a mechanical stirrer, gas inlet tube extending below the solvent surface and a water condenser with a gas outlet. The system was flushed with acetylene gas (bubbled through an activated aluminum oxide trap, two concentrated sulfuric acid traps and an empty trap for 3 min. Carbon tetrachloride (70 ml) was added to the flask and the system flushed with acetylene for 3 min. The flask was cooled in an ice-water bath and 8.3 g (0.053 mole) of anhydrous aluminum chloride was added. The system was flushed with acetylene for 3 min. The gas inlet was replaced with an addition funnel and 8.3 g (0.053 mole) of spiro[3.3]heptane-3-carboxylic acid chloride was added slowly over a 10 min. period. The addition funnel was replaced with the gas inlet tube and acetylene was bubbled through the mixture for 4 hr. The mixture was poured into 100 ml of crushed ice and 150 ml of saturated sodium chloride solution. The phases were separated and the aqueous material was extracted with 195 ml (3×65 ml) of ether. The combined organic extracts were washed with 150 ml (3×50 ml) of 10% (v/v) aqueous hydrochloric acid solution, 150 ml (3×50 ml) of saturated sodium bicarbonate solution and 100 ml of saturated sodium chloride solution. The material was dried over anhydrous magnesium sulfate, filtered and the solvents were removed in vacuo. The material was distilled at reduced pressure to yield 7.3 g (75.7%) of 1-chloro-3-(spiro[3.3]hept-2-yl)-1E-propen-3-one.

Analysis — b.p.65°–68° C/0.2 mm.
NMR(CDCl$_3$): $\delta$1.5–2.5, multiplet, 10H; $\delta$3.3, multiplet, 1H; $\delta$6.4, doublet, 1H J=14HZ; $\delta$7.2 ppm, doublet, 1H J=14Hz.

H. Preparation of 1-Iodo-3-(spiro[3.3]hept-2-yl)-1E-propen-3-one

1-Chloro-3-(spiro[3.3]hept-2-yl)-1E-propen-3-one (7.3 g, 0.042 mole) was mixed with 25.2 g (0.168 mole) of sodium iodide and 45 ml of dry acetone (distilled from anhydrous potassium carbonate, b.p. 56° C). The mixture was refluxed with rapid stirring overnight. The mixture was cooled and the solvent was removed in vacuo. The solid residue was taken up in 75 ml of water and the products were extracted with 150 ml (3×50 ml) of ether. The organic material was washed with 50 ml of saturated sodium bicarbonate solution, 50 ml of aqueous sodium thiosulfate solution and 50 ml of saturated sodium chloride solution. The material was dried over anhydrous magnesium sulfate, filtered and the solvent was removed in vacuo to yield 6.9 g (62.2%) of crude 1-iodo-3-(spiro[3.3]hept-2-yl)-1E-propen-3-one.

Analysis — NMR(CDCl$_3$): $\delta$1.5–2.4, multiplet, 10H; $\delta$3.3, multiplet, 1H; $\delta$6.9, doublet, 1H, J=15HZ; $\delta$7.5 ppm, doublet, 1H, J=15HZ.

I. Preparation of 1-Iodo-3-(spiro[3.3]hept-2-yl)-1E-propen-3RS-ol

1-Iodo-3-(spiro[3.3]hept-2-yl)-1E-propen-3-one (8.62 g, 0.0311 mole) was dissolved in 100 ml of absolute ethanol and the mixture cooled to −20° C. Sodium borohydride (4.71 g, 0.124 mole) was dissolved in 100 ml of absolute ethanol and added to the cooled mixture. The mixture was allowed to stir for 1 hr at 0° C. The solvent was removed in vacuo and the residue was taken up in 250 ml of water. The products were extracted with 300 ml (3×100 ml) of ether. The extracts were washed with 75 ml of saturated sodium chloride solution, dried over anhydrous magnesium sulfate, filtered and the solvent removed in vacuo to yield 7.5 g of 1-iodo-3-(spiro[3.3]hept-2-yl)-1E-propen-3RS-ol.

Analysis — NMR(CDCl$_3$): $\delta$1.5–2.5, multiplet, 11H; $\delta$3.8, multiplet, 1H; $\delta$6.0–6.5 ppm, multiplet, 2H.

J. Preparation of 1-Iodo-3RS-(1-ethoxyethoxy)-3-(spiro[3.3]hept-2-yl)-1E-propene.

1-Iodo-3-(spiro[3.3]hept-2-yl)-1E-propen-3RS-ol (7.5 g, 0.027 mole) was mixed with 38.2 g (50 ml, 0.512 mole) of ethylvinyl ether. Phosphorous oxychloride (2 drops) was added and the mixture was allowed to stir overnight at room temperature. The mixture was poured into 75 ml of saturated sodium bicarbonate solution and the products were extracted with 100 ml (2×50 ml) of ether. The organic material was washed with 50 ml of saturated sodium chloride solution, dried over anhydrous magnesium sulfate, filtered and the solvent was removed in vacuo. Chromatography was preformed on silica gel 60 (0.063–0.2 mm, 70–230 mesh, ASTM) using benzene elutant to yield 5.3 g (56.4%) of 1-iodo-3RS-(1-ethoxyethoxy)-3-(spiro[3.3]hept-2-yl)-1E-propene.

Analysis — NMR(CDCl$_3$): $\delta$0.8–25, multiplet, 17H; $\delta$3.5, multiplet, 3H; $\delta$4.6, quartet, 1H, J=5HZ; $\delta$6.3 ppm, multiplet, 2H.

EXAMPLE 10

This Example illustrates the preparation of the intermediate compound 1-iodo-3RS-(1-ethoxyethoxy)-3-(spiro[5.5]undec-3-yl)-1E-propene using the following procedure.

A. Preparation of Spiro[5.5]undecane-3-carboxylic acid chloride

In a procedure as described in Example 9F, spiro[5.5]undecane-3-carboxylic acid chloride was prepared from thionyl chloride and spiro[5.5]undecane-3-carboxylic acid (preparation described in U.S. Pat. No. 3,350,442).

Analysis — NMR(CDCl$_3$): $\delta$0.6–2.4, multiplet, 18H.

B. Preparation of 1-Chloro-3-(spiro[5.5]undec-3-yl)-1E-propen-3-one

In a procedure as described in Example 9G, 1-chloro-3-(spiro[5.5]undec-3-yl)-1E-propen-3-one was prepared from anhydrous aluminum chloride, spiro[5.5]undecane-3-carboxylic acid chloride and acetylene. The compound was purified by column chromatography on silica gel 60 (0.063–0.2 mm, 70–230 mesh, ASTM) using chloroform as the solvent.

Analysis — NMR(CDCl$_3$): $\delta$0.6–2.6, multiplet, 19H; 6.5, doublet, 1H, J=15HZ; 7.3 ppm, doublet, 1H, J=15Hz.

C. Preparation of 1-Iodo-3-(spiro[5.5]undec-3-yl)-1E-propen-3-one

In a procedure as described in Example 9H, 1-chloro-3-(spiro[5.5]undec-3-yl)-1E-propen-3-one was reacted with sodium iodide in acetone to yield 1-iodo-3-(spiro[5.5]undec-3-yl)-1E-propen-3-one (70.9%).

Annalysis — NMR(CDCl$_3$): $\delta$0.8–2.5, multiplet, 19H; $\delta$7.22, doublet, 1H, J=16HZ; $\delta$7.85 ppm, doublet, 1H, J=16HZ.

D. Preparation of 1-Iodo-3-(spiro[5.5]undec-3-yl)-1E-propen-3RS-ol

In a procedure as described in Example 9I, 1-iodo-3-(spiro[5.5]undec-3-yl)-1E-propen-3-one was reduced with sodium borohydride in ethanol to yield 1-iodo-3-(spiro[5.5]undec-3-yl)-1E-propen-3RS-ol (98.5%).

Analysis — NMR(CDCl$_3$): $\delta$0.5–2.2, multiplet, 19H; $\delta$3.95, multiplet, 1H; $\delta$6.1–6.8 ppm, multiplet, 2H.

E. Preparation of 1-Iodo-3RS-(1-ethoxyethoxy)-3-(spiro[5.5]undec-3yl)-1E-propene.

In a procedure as described in Example 9J, 1-iodo-3RS-(1-ethoxyethoxy)-3-(spiro[5.5]undec-3-yl)-1E-propene was prepared from 1-iodo-3-(spiro[5.5]undec-3-yl)-1E-propen-3RS-ol and ethylvinyl ether using phosphorous oxychloride as a catalyst. The compound was obtained in 76.9% yield.

Analysis — NMR(CDCl$_3$): $\delta$0.7–2.1, multiplet, 25H; $\delta$3.6, multiplet, 3H; $\delta$4.7, quartet, 1H, J = 6Hz; $\delta$6.1–6.6 ppm, multiplet, 2H.

EXAMPLE 11

Preparation of Compounds TR-4758 and TR-4759

Repeating in a similar manner the procedure of Example 7, but replacing 1-tetrahydropyran-2-yloxy-7-

{3R-(tetrahydropyran-2-yloxy)-5-oxocyclopent-1-enyl}heptane with methyl 7-(6-oxocyclohex-1-enyl)-hept-5Z-enoate yields the 9a-homo prostaglandin $E_2$ analogues TR-4758 and TR-4759.

A. Compound TR-4759 had the following spectral properties;

Analysis — IR$\lambda_{max}^{CHCl_3}$: 2.78, 2.85(broad), 3.4, 5.80, 5.85, 10.40μ.

NMR(CDCl$_3$): δ3.66, singlet, 3H; 3.92, multiplet, 1H; 5.40, multiplet, 4H.

Ms(70eV): m/e388(p); 370(p-H$_2$O); 357(p-OCH$_3$); 352(p-2H$_2$O).

B. Compound TR-4758 had the following spectral properties:

Analysis — IR, NMR and Ms are essentially the same as compound TR-4759 above.

EXAMPLE 12

Preparation of compounds TR-4841 and TR-4852

Repeating in a similar manner the procedure of Example 7, but replacing 1-iodo-3RS-(1-ethoxyethoxy)-3-(spiro[3.3]hept-2-yl)-1E-propene with 1-iodo-3RS-(tetrahydropyran-2-yloxy)-3-(2-methylspiro[3.3]hept-2-yl)-1E-propene yields the prostaglandin analogues TR-4841 and TR-4852.

A. Compound TR-4841 had the following spectral properties:

Analysis — IR$\lambda_{max}^{CHCl_3}$: 2.78, 2.88(broad), 5.75, 10.4μ.

NMR(CDCl$_3$): δ1.00, singlet, 3H; 3.60, triplet, J=5.0Hz, 2H; 4.0, multiplet, 2H; 5.67, multiplet, 2H.

$[\alpha]_D$(CHCl$_3$,c0.89) −53.8°

Ms (70eV) m/e: 360(p-H$_2$O); 342(p-2H$_2$O); 269(p-C$_8$H$_{13}$).

B. Compound TR-4852 had the following spectral properties:

Analysis — IR$\lambda_{max}^{CHCl_3}$: 2.78, 2,94(broad), 10.4μ

NMR(CDCl$_3$): δ1.08, singlet, 3H; 3.10, broad singlet, 3H; 3.65, broad triplet, 2H; 3.90, multiplet, 2H; 5.60, multiplet, 2H.

$[\alpha]_D$(CHCl$_3$,c0.89) −43.8°

Ms (70eV) m/e: 360(p-H$_2$O); 342(p-2H$_2$O); 269(p-C$_8$H$_{13}$); 251(p-C$_8$H$_{13}$-H$_2$O).

EXAMPLE 13

Preparation of compounds TR-4842 and TR 4845

Repeating in a similar manner the procedure of Example 1, but replacing 1-iodo-3RS-(1-ethoxyethoxy)-3-(spiro[3.3]hept-2-yl)-1E-propene with 1-iodo-3RS-(tetrahydropyran-2-yloxy)-3-(2-methylspiro[3.3]hept-2-yl)-1E-propene yields prostaglandin analogues TR-4842 and TR-4845.

A. Compound TR-4842 had the following spectral properties:

Analysis — IR: $\lambda_{max}^{CHCl_3}$: 2.78, 2.90, 5.75, 10.4μ.

NMR(CDCl$_3$): δ1.02, singlet, 3H; 3.66, singlet, 3H; 4.02, multiplet, 2H; 5.65, multiplet, 2H.

$[\alpha]_D$(c0.87,CHCl$_3$) −64.1°.

Ms (70eV) m/e:388(p-H$_2$O); 339(p-2H$_2$O—OCH$_3$); 317(p-OCH$_3$—C$_5$H$_8$); 297(p-C$_8$H$_{13}$).

B. Compound TR-4845 had the following spectral properties;

Analysis — IR, Ms spectra essentially the same as for compound TR-4842 above.

NMR (CDCl$_3$): δ1.08, singlet, 3H; 3.66, singlet, 3H; 3.96, multiplet, 2H; 5.60, multiplet, 2H.

$[\alpha]_D$(c0.86, CHCl$_3$) −44.8°.

EXAMPLE 14

This Example illustrates the preparation of the intermediate compound 1-iodo-3RS-(tetrahydropyran-2-yloxy)-3-(2-methylspiro[3.3]hept-2-yl)-1E-propene using the following procedure.

A. Preparation of 2-Methylspiro[3.3]heptane-2-carboxylic acid

A slurry of 2.15 g (44.2 mmol) of sodium hydride (50% in oil) in 45.0 ml of dry THF was stirred under argon at −20° C. A solution of 5.52 g (40.0 mmol) of spiro[3.3]heptane-2-carboxylic acid in 5.0 ml of dry THF was added dropwise. The reaction mixture was stirred for 0.5 hr at −20° C. A solution of 44.5 mmol of freshly-prepared, −20° C lithium diisopropylamide in 31.0 ml of THF was added to the reaction mixture. The reaction mixture was stirred for 0.3 hr at 0° C. Methyl iodide (2.80 ml, 44.5 mmol) was added, and the reaction mixture stirred an additional 2.0 hr at 25° C. The reaction mixture was cooled to −20° C and the reaction quenched by careful addition of cold 10% aqueous HCl. The mixture was extracted with 1:1 ethylacetate-ether. The extracts were washed with brine, then dried (MgSO$_4$), filtered, and solvents evaporated in vacuo. The residue was dissolved in 1 N NaOH and extacted three times with ether. The aqueous layer was acidified with 6 N HCl and extracted with 1:1 ethyl-acetate-ether. These extracts were washed with brine, dried (MgSO$_4$), filtered and evaporated in vacuo to yield 5.1 g of 2-methylspiro[3.3]heptane-2-carboxylic acid as a light yellow oil (82.5%).

Analysis — NMR (CHCl$_3$): δ1.35, singlet, 3H; 11.4, broad singlet, 1H.

B. Preparation of 2-Methyl-2-acetylspiro[3.3]heptane.

A solution of 5.0 g (33.0 mmol) 2-methylspiro[3.3-]heptane-2-carboxylic acid in 33.0 ml of dry ether was stirred under argon at 0° C and 47.6 ml (74.3 mmol) of 1.56 M methyl lithium in ether added dropwise. The reaction mixture was allowed to warm to 25° C and was stirred for 3.0 hr. The reaction mixture was cooled to −20° C and quenched by addition of 10% aqueous HCl. The layers were separated and the aqueous layer extracted with ether. The combined organic layers were washed with saturated aqueous sodium bicarbonate and brine, then dried (MgSO$_4$), filtered, and evaporated in vacuo to afford 2-methyl-2-acetylspiro[3.3]heptane as a light yellow oil (4.91 g 98%).

Analysis — NMR (CDCl$_3$): δ1.35, singlet, 3H; 2.0, singlet, 3H.

IR: $\lambda_{max}^{CHCl_3}$ 3.85, 7.40, 8.80μ.

C. Preparation of (2-Methylspiro[3.3]hept-2-yl) (2-hydroxyvinyl)ketone

A solution of 7.8 g (130.0 mmol) methyl formate and 4.91 g (32.4 mmol) of 2-methyl-2-acetylspiro[3.3]heptane in 8.0 ml of dry ether was dropped into a slurry of 1.2 g of sodium hydride in 180 ml of ether. A few drops of MeOH were added and the reaction mixture stirred for 1.5 hr at 25° C. The reaction mixture was cooled to −10° C and the reaction quenched by slow addition of water. The layers were separated and the aqueous layer extracted twice with ether. The combined organic extracts were washed with water and 1 N NaOH. The combined aqueous layers were acidified with 6 N HCl and extracted with ether. The ether extracts were washed with brine, then dried (MgSO$_4$), filtered and evaporated in vacuo to yield 4.0 g of of (2-methylspiro[3.3-]hept-2-yl)(2-hydroxyvinyl)heptane as a yellow oil (69.5%).

Analysis — IR: $\lambda_{max}^{CHCl_3}$: 3.85, 7.40, 8.80μ.

NMR (CDCl$_3$) δ 1.32, singlet, 3H; 5.5, doublet, J=4.0Hz, 1H; 7.90, doublet, J=4.0Hz, 1H; 8.05, singlet, 1H.

D. Preparation of 1-Chloro-3-(2-methylspiro[3.3]hept-2-yl)-1E-propen-3-one

A solution of 4.0 g of (2-methylspiro[3.3]hept-2-yl) (2-hydroxyvinyl) ketone in 25.0 ml of benzene was added dropwise with stirring to 3.95 g of thionyl chloride. The reaction mixture was allowed to stand for 18 hr at 25° C. The product was isolated by distillation (high vacuum) to afford 2.66 g 1-chloro-3-(2-methylspiro[3.3]hept-2-yl)-1E-propen-3-one as a yellow oil (40%).

Analysis — bp 65°-75° C; R$_f$(CHCl$_3$) 0.21.

E. Preparation of 1-Iodo-3-(2-methylspiro[3.3]hept-2-yl)-1E-propen-3-one

In a procedure as described in Example 9H, 1-chloro-3-(2-methylspiro[3.3]hept-2-yl)-1E-propen-3-one was reacted with sodium iodide in acetone to yield 1-iodo-3-(2-methyspiro[3.3]hept-2-yl)-1E-propen-3-one (87%).

Analysis — NMR (CDCl$_3$) δ1.32, singlet, 3H; 7.22, doublet, J=14Hz, 1H; 7.85, doublet, J=14Hz, 1H.

F. Preparation of 1-Iodo-3RS-hydroxy-3-(2-methylspiro[3.3]hept-2-yl)-1E-propene

In a procedure as described in Example 9I, 1-iodo-3-(2-methylspiro[3.3]hept-2-yl)-1E-propen-3-one was reduced with sodium borohydride in ethanol to yield 1-iodo-3RS-hydroxy-3-(2-methylspiro[3.3]hept-2-yl)-1E-propene (100%).

Analysis — NMR (CDCl$_3$): δ1.35, singlet, 3H; 3.3–4.0, multiplet, 2H; 6.35, multiplet, 2H.

IR: $\lambda_{max}^{CHCl_3}$ 2.78, 2.95(broad), 6.20, 7.25, 7.25, 10.3, 10.5μ.

G. Preparation of 1-Iodo-3RS-(tetrahydropyran-2-yloxy)-3-(2-methylspiro[3.3]hept-2-yl)-1E-propene.

Crude 1-iodo-3RS-hydroxy-3-(2-methylspiro[3.3-]hept-2-yl-1E-propene (3.31 g) was dissolved in 12.0 ml dry ether and stirred under argon at 25° C. Distilled dihydropyran (1.25 ml) was added, followed by a small spatula of p-tolunesulfonic acid. The reaction mixture was allowed to stand for 2 hr at 25° C, then partitioned between ether and saturated aqueous NaHCO$_3$. The organic layer was dried (MgSO$_4$), filtered, and evaporated in vacuo to afford 4.43 g crude 1-iodo-3RS-(tetrahydropyran-2-yloxy)-3-(2-methylspiro[3.3]hept-2-yl)-1E-propene as a crude orange oil. Purification by column chromatography on Silica Gel afforded 2.90 g of the compound as a clear oil.

Analysis — NMR (CDCl$_3$): δ1.32, singlet, 3H; 3.50, multiplet, 1H; 3.75, multiplet, 2H; 4.60, broad singlet, 1H.

EXAMPLE 15

A. Evaluation of Inhibition of Human Platelet Aggregation by Analogues of Prostaglandins Structure III The ability of test compounds to inhibit platelet aggregation was determined by a modification of the turbidometric technique of Born (Nature, 194:927 [1962]). Blood was collected from human volunteers who had not ingested aspirin or aspirin-containing products within the preceding two weeks in heparinized containers and was allowed to settle for one (1) hour. The platelet rich plasma (prp) supernates were collected and cooled. Siliconized glassware was used throughout.

In a representative assay 1.9 ml of PRP and 0.2 ml of test compound at the appropriate concentrations (0.001 to 100 mcgm), or 0.2 ml of distilled water (control procedure) were placed in sample cuvettes. The cuvettes were placed in a 37° C incubation block for 15 minutes, and then in a spectrophotometer linked to a strip chart recorder. After 30–60 seconds, 0.2 ml of a solution, prepared by diluting a calf-skin collagen solution 1:9 with Tyrodes' Solution, was added to each cuvette. Platelet aggregation was evidenced by a decrease in optical density.

Calculation of the degree of inhibition of platelet aggregation exhibited by each concentration of test compound was accomplished according to the method of Caprino et al., (Arzneim-Forsch., 23:1277 [1973]). An ED$_{50}$ value was then determined graphically. Activity of the compounds was scored as follows:

| ED$_{50}$(mcg/kg) | Activity Value |
|---|---|
| No activity | 0 |
| >1.0 | 1 |
| >0.1 ≤ 1.0 | 2 |
| >0.01 ≤ 0.1 | 3 |
| >0.001 ≤ 0.01 | 4 |
| ≤ 0.001 | 5 |

B. Evaluation of the Effects of Prostaglandin Analogues III on Gastric Secretion in the Rat A procedure based on that described by Lipmann (J. Pharm. Pharmacol., 21:335 [1968]) was used to assess the influence of test compounds on gastric secretion. Rats of one sex weighing 150 to 200 g were randomly divided into groups of six animals each and fasted for 48 hours previously to the experiments, water being available adlibitum. The animals were anesthetized with ether, the abdomen was opened through a midline incision and the pylorus was ligated. Test compounds were diluted from stock solution so as to administer a dose of 1.5 mg/kg in a volume equivalent to 1 ml/kg. Subcutaneous injections were applied immediately after surgery and again 2 hours later, so that a total dose of 3.0 mg/kg was administered. Dilutions were made with phosphate buffer (pH 7.38) as recommended by Lee et al. (Prostaglandins 3:29 [1973]), in order to insure adequate stability of drugs at the subcutaneous depot. Each compound was tested in one group of rats; an additional control group received only the vehicle.

Four hours after pyloric ligation the animals were killed with ether, the cardias ligated and the stomachs removed. The volume of gastric secretion was measured and the contents centrifuged at 500 rpm for 10 minutes. Total acid in the supernatant was titrated against a 0.1 N sodium hydroxide solution and the amount expressed in mEq.

Volume and total acid values of the treated group were compared with those of the controls by the "T" test. Antisecretory activity was scored according to the following scale:

| % decrease in acidity | Activity Value |
|---|---|
| <26 | 0 |
| 26–50, not significant | 1 |
| 26–50, significant | 2 |
| 51–75 | 3 |
| 76–100 | 4 |

C. Evaluation of the Effects of Prostaglandin Analogues III on Femoral Blood Flow in the Dog The peripheral vasodilator or constrictor effects of these compounds were determined in mongrel dogs of either sex, weighing between 10 and 20 kg anesthestized intravenously with 35 mg/kg of sodium pentobarbital. An external iliac artery was dissected immediately above the femoral arch for a length of approximately 5 cm and a previously calibrated, non-connulating electromagnetic flowmeter sensor with a lumen between 2.5 and 3.5 mm was placed snugly around the vessel. Cannulas were placed in a branch of the artery arising distally to the location of the flowmeter sensor for intraarterial drug administrations, in the contralateral femoral artery for systemic blood pressure recordings and in the trachea for artificial respiration with room air. Femoral blood flow and systemic blood pressure were continously recorded with an electromagnetic flowmeter and pressure tranducer, respectively.

After an adequate control period, test compounds were injected intraarterially at one log-spaced doses ranging from 0.001 to 10 mcg., in a volume of 0.5 ml and at 5 to 10 minute intervals. Maximum changes in bloodflow, as well as any variations in blood pressure, were tabulated for each dose in absolute values (ml/min. and mmHg). The calculations were made taking as control values those existing immediately before administration of each dose. The direction of the observed change (plus for increase and minus for decrease) was also noted. The dose changing bloodflow by 100 ml/min ($ED_{100}$ml/min) was calculated graphically and was used for scoring activity as follows:

| $ED_{100}$ml/min, mcg | Activity Value |
|---|---|
| >10.0 | 0 |
| 1.01 – 10.0 | 1 |
| 0.11 – 1.0 | 2 |
| 0.01 – 0.1 | 3 |

D. Evaluation of the Effects of Prostaglandin Analogues III on Blood Pressure and Heart Rate in the Anesthetized Cat The acute effects of test compounds on blood pressure and heart rate were determined in cats of either sex anesthetized with a mixture of pentobarbital sodium (35 mg/kg, i.v.) and barbital sodium (100 mg/kg, i.v.). Cannulas were placed in the trachea to allow adequate spontaneous ventilation, in a femoral artery for blood pressure recording with a strain gage transducer, and in a saphenous vein for drug administration. Heart rate was recorded by means of a cardiotachometer driven by the R wave of the electrocardiogram. After a period of 10 minutes of stable recordings of blood pressure and heart rate, the test compound was administered intravenously at doses increasing from 0.01 to 10.0 mcg/kg, spaced one log and injected at 10 minutes intervals. All doses were injected in a volume of 0.1 ml/kg. Modifications of blood pressure and heart rate induced by the test compound were expressed both in absolute units (mmHg and beats/minutes) and as percent of values recorded immediately before administration of each dose. Biphasic responses were tabulated in the order in which they occur. The direction of the observed changes was also noted (+ for increases and − for decreases).

Activity of compounds in this test was judged only on the basis of the degree of hypotension observed. Thus, the $ED_{50}$ mmHg (dose decreasing blood pressure by 50 mmHg) was calculated graphically and the compound scored according to the following scale:

| $ED_{50}$ mmHg, mcg/kg | Activity Value |
|---|---|
| >10.0 | 0 |
| 1.01 – 10.0 | 1 |
| 0.11 – 1.0 | 2 |
| 0.01 – 0.1 | 3 |

Table D summarizes the results of the preceding assays A to D utilizing the preferred examples.

TABLE D

Summary of Activity of Prostaglandin Analogues III in; Test A: Inhibition of Human Platelet Aggregation; Test B: Inhibition of Rodent Gastric Secretion; Test C: Increase in Canidae Femoral Blood Flow; and Test D: Decrease in Normal Feline Blood Pressure and Heart Rate

TABLE D

| TR No. | Example No. | Activity Value | | | |
|---|---|---|---|---|---|
| | | Test A | Test B | Test C | Test D |
| 4126 | 2A | 1 | NT | NT | 0 |
| 4127 | 2B | 1 | NT | NT | 0 |
| 4120 | 1A | 3 | 2 | 0 | 0 |
| 4121 | 1B | 1 | 1 | 2 | 0 |
| 4020 | 5A | 1 | 0 | 0 | 0 |
| 4021 | 5B | 1 | 0 | 0 | 0 |
| 4136 | 4A | 1 | 1 | 0 | 0 |
| 4137 | 4B | 1 | 3 | 3 | 2 |
| 4146 | 6A | 1 | 0 | 0 | 0 |
| 4147 | 6B | 1 | 0 | 0 | 2 |
| 4139 | 3A | 1 | 0 | 0 | 0 |
| 4138 | 3B | 1 | NT | NT | 0 |
| 4713 | 7A | 1 | 4 | NT | NT |
| 4714 | 7B | 1 | 0 | NT | NT |
| 4841 | 12A | 1 | 0 | NT | NT |
| 4852 | 12B | 1 | 2 | NT | NT |
| 4842 | 13A | 1 | 0 | NT | NT |
| 4845 | 13B | 3 | 3 | NT | NT |
| 4726 | 8A | 1 | 0 | NT | NT |
| 4727 | 8B | 1 | 0 | NT | NT |
| 4758 | 11B | 1 | 0 | NT | NT |
| 4759 | 11A | 1 | 0 | NT | NT |

NT: Not tested

E. Evaluation of Cascade Assay Effects by Analogues of Prostaglandin Structure III The smooth muscle stimulant effects of test compounds were determined simultaneously in four different tissues that are known to be reactive to naturally occurring prostaglandins. Segments of rat stomach fundus, rat colon, chick rectum and rabbit aortic strip were obtained as described by: Vane, J. R., Brit. J. Pharmacol., 12: 344 (1957); Regoli, D. and Vane, J. R., Brit. J. Pharmacol., 23: 351 (1964); Mann, M. and West, G.

B., Brit. J. Pharmacol., 5: 173 (1950); and Furchgott, R. F. and Bhadrakom, R., J. Pharmacol. Exper. Ther., 108: 129 (1953). One end of each preparation was tied to the bottom of a 10 ml tissue chamber and the other to a force displacement transducer (Grass FT-03) for continuous tension recording. The stomach, colon, and rectum segments were stretched to an initial tension of 1 g, while the aortic strip was subjected to 4 g. All preparations were left undisturbed for 1 hour prior to testing. The chambers were equipped with an external jacket through which water, maintained at 40° C, was circulated. Preparations were arranged one beneath the other in descending order (aorta, stomach, colon and rectum). Provision was made for bathing the four tissues successively so that they were superfused with the same fluid (Gaddum, H. J., Brit. J. Pharmacol., 6: 321 [1953]. The bathing fluid consisted of: Krebs bicarbonate solution aerated with a mixture of 95% $O_2$ and 5% $CO_2$ and warmed at 37° C; atropine sulphate (0.1 mcg/ml), phenoxybenzamine hydrochloride (0.1 mcg/ml), propranolol hydrochloride (3.0 mcg/ml), methysergide maleate (0.2 mcg/ml) and brompheniramine maleate (0.1 mcg/ml) were added to eliminate the possibility of smooth muscle responses being due to stimulation of cholinergic, adrenergic, serotonin or histamine receptors. The fluid was circulated by means of a roller pump and was allowed to drip over the preparations at a rate of 10 ml/minute.

Test compounds were diluted from stock solutions so as to administer quantities ranging from 0.001 100,000 ng in a volume of 0.5 ml. The compounds were applied by dripping on the uppermost tissue, at intervals of 10 to 20 minutes. Maximal increases in tension after each dose were measured and the results were used to plot dose-response curves. $ED_{50}$ data (doses necessary to produce a response 50% of maximum) were then calculated graphically for each tissue. Maximum responses utilized were those elicited by $PGE_1$ in gastric and rectal tissue, by $PGF_{2\alpha}$ in colonic tissue, and by $PGA_2$ in aortic tissue.

Activity in each tissue was scored according to the following scale:

| $ED_{50}$, ng | Activity Value |
|---|---|
| >10000 | 0 |
| 1001 – 10000 | 1 |
| 101 – 1000 | 2 |
| 10 – 100 | 3 |
| <10 | 4 |

F. Evaluation of the Effects on the Rat Uterus in Vitro by Analogues of Prostaglandin Structure III The uterine stimulant effect of test compounds was determined in segments of uterus obtained from rats (140–160 g) pretreated subcutaneously with 1 mg/kg of diethyl-stilbesterol 18 hours before the experiment. The tissues were placed in 10 ml chambers filled with de-Jalon solution at 29° C, were aerated and bubbled with 95% $O_2$ and 5% $CO_2$, and were prepared for isometric recording with force displacement transducers. Preparations were stretched to an initial tension of 1 g and were left undisturbed for 30 minutes. Carbachol (1 mcg/ml) was then added to the bath and a response was recorded. After a 10 minute interval the carbachol procedure was repeated. Responses to increasing concentrations of a test compound (0.001 to 10 mcg/ml with one log intervals) were then recorded every 10 minutes. Preparations were washed four times after each response. All doses of compounds were administered in a 0.1 ml volume. Because it has been observed that the magnitude of the second response to carbachol (approximately 10% greater than the first) is close to the maximal response of the tissue, such value was taken as a measure of the sensitivity of a particular segment. Responses to each concentration of the test compound were expressed in terms of percentage of the second response to carbachol and the $ED_{50}$ (dose producing a response 50% that of carbachol) was calculated graphically. Activity was scored according to the following scale:

| $ED_{50}$ (mcg/ml) | Activity Value |
|---|---|
| >10 | 0 |
| 1.001 – 10 | 1 |
| 0.101 – 1.0 | 2 |
| 0.01 – 0.1 | 3 |
| <0.01 | 4 |

G. Evaluation of the Effects on the Guinea Pig Trachea in Vitro by Analogues of Prostaglandin Structure III A male guinea pig weighing 200–500 g was killed by a blow on the head. A 20 mm length of the trachea was dissected from the animal, transferred to a petri dish containing Krebs' solution (aerated with 95% $O_2$ and 5% $CO_2$ at 37° C), and cut longitudinally opposite the tracheal muscle. The tissue was then cut transversely three quarters of the distance across, a second cut in the opposite direction (again three quarters of the distance across the tissue) was made and the procedure was continued for the whole tissue. The ends of the trachea were pulled to form a zig-zag shaped strip. The tracheal strip used in the experiment was approximately 30 mm when extended under 0.25–0.5 g load in the tissue bath. Cotton thread was tied to one end of the tissue, and linen thread to the other. It was attached via the linen thread to a glass hook in a 5 ml isolated tissue bath containing Krebs' solution (37° C, aerated with a mixture of 95% $O_2$ and 5% $CO_2$). The opposite end was attached via cotton to an isotonic Harvard transducer (Model 386 Heart/Smooth Muscle Transducer, Harvard Apparatus). The load on the transducer lever was small, usually 0.3 g, with a range of 0.25–0.5 g, and the magnification high, 80 fold using an appropriate twin-channel pen recorder. A minimum of 30 minutes was allowed before applying a test compound to the tissue. Test compounds were then applied (in volumes of 0.5 ml) at 30 minute intervals, being in contact with the tissue for 5 minutes followed by an overflow washout time of 20 seconds.

Prostaglandin $E_1$, at a bath concentration of 0.1 mcg/ml, was then tested repeatedly on two such strips, obtained from two different animals, until two responses (the values of which are recorded) differing by no more than 25% occur. A test compound was then added to the same two strips at bath concentrations of 0.01, 0.1, 1.0, and 10.0 mcg/ml and the effects of the compound were recorded. After the test compound had been evaluated at the highest concentration, $PGE_1$ was retested at 0.1 mcg/ml (and the value of the response recorded) to insure that the viability of the strips was retained during the experiment. The mean of the effects of the test compound on the two strips was then calculated for each concentration, and, based on the resulting values, an activity value was assigned as follows:

| Response | Activity Value |
| --- | --- |
| More relaxation at 0.01 mcg/ml than that elicited by $PGE_1$ | R4 |
| More relaxation at 0.1 mcg/ml than that elicited by $PGE_1$ | R3 |
| More relaxation at 1.0 mcg/ml than that elicited by $PGE_1$ | R2 |
| More relaxation at 10.0 mcg/ml than that elicited by $PGE_1$ | R1 |
| No effect at any concentration greater than that elicited by $PGE_1$ | 0 |
| More contraction at 10.0 mcg/ml than the degree of relaxation elicited by $PGE_1$ | C1 |
| More contraction at 1.0 mcg/ml than the degree of relaxation elicited by $PGE_1$ | C2 |
| More contraction at 0.1 mcg/ml than the degree of relaxation elicited by $PGE_1$ | C3 |
| More contraction at 0.01 mcg/ml than the degree of relaxation elicited by $PGE_1$ | C4 |

H. Evaluation of Antagonistic Effects on the Guinea Pig Ileum in Vitro by Analogues of Prostaglandin Structure III The degree and specificity of antagonism of test compounds to the smooth muscle stimulant effects of prostaglandins were assessed in segments of terminal guinea pig ileum. Preparations were placed in tissue chambers filled with Ringer-Tyrode solution at 37° C, bubbled with a mixture of 95% $O_2$ and 5% $CO_2$, and arranged for isometric recording with force displacement transducers. The segments were stretched to an initial tension of 1 g, and responses to a test concentration of acetylcholine (0.1 mcg/ml) were obtained every 5 minutes until two similar responses were observed (usually after four administrations). Responses to acetylcholine (0.1 mcg/ml), $PGE_1$ (0.1 mcg/ml), $BaCl_2$ (100 mcg/ml) and $PGF_{2\alpha}$ (1 mcg/ml) were obtained (and recorded) in that order at 5 minute intervals before and after 100 seconds of incubation with 0.1 and 1.0 mcg/ml of the test compound. Any direct contractile effect of the test compound was recorded and evaluated in terms of mean values in grams of tension developed at each concentration. Responses to the different agonists observed after incubation with the test compound were expressed as percent of control responses. All drugs were administered in a volume of 0.1 ml.

Antagonism to prostaglandins was scored independently for $PGE_1$ and $PGF_{2\alpha}$ according to the following criteria:

| Response | Activity Value |
| --- | --- |
| Less than 50% blockade of PG response | 0 |
| More than 50% blockade of PG responses and more than 10% antagonism of Ach and/or $BaCl_2$, or production of direct contraction | 1 |
| More than 50% blockade of PG responses at 1 mcg/ml with less than 11% antagonism of Ach and $BaCl_2$ without production of direct contraction | |

Table E summarizes the results of the preceding assays E to H utilizing the preferred examples.

TABLE E

Summary of Activity of Prostaglandin Analogues III in:
Test E: Cascade Assay
Test F: Rat Uterus
Test G: Guinea Pig Trachea
Test H: Antagonistic Effects on Guinea Pig Ileum

| TR No. | Ex. No. | Test E Stomach | Colon | Rectum | Aorta | Test F | Test G | Test H Antagonism $PGE_1$ | $PGF_{2\alpha}$ |
| --- | --- | --- | --- | --- | --- | --- | --- | --- | --- |
| 4126 | 2A | 0 | 0 | 0 | 0 | NT | C1 | 0 | 1 |
| 4127 | 2B | 0 | 0 | 0 | 0 | 0 | C1 | 0 | 1 |
| 4120 | 1A | 0 | 0 | 1 | 0 | 0 | C4 | 0 | 0 |
| 4121 | 1B | 0 | 0 | 0 | 0 | 0 | C1 | 0 | 0 |
| 4020 | 5A | 2 | 0 | 0 | 0 | 0 | R0 | 0 | 0 |
| 4021 | 5B | 4 | 0 | 0 | 0 | 0 | C0 | 0 | 0 |
| 4136 | 4A | 2 | 0 | 1 | 0 | 0 | C2 | 0 | 0 |
| 4137 | 4B | 1 | 0 | NT | 0 | 0 | C1 | 0 | 0 |
| 4146 | 6A | 1 | 2 | NT | 0 | 0 | C0 | 0 | 0 |
| 4147 | 6B | 2 | 0 | 2 | 1 | 0 | R0 | 0 | 1 |
| 4139 | 3A | 0 | 0 | 0 | 0 | 0 | C1 | 0 | 0 |
| 4138 | 3B | 0 | 0 | 0 | 0 | 0 | C1 | 0 | 0 |
| 4713 | 7A | 0 | 0 | 1 | 0 | 0 | C1 | 0 | 0 |
| 4714 | 7B | 0 | 0 | 0 | 0 | 0 | C1 | 0 | 0 |
| 4841 | 12A | 0 | 0 | 0 | 0 | 0 | C0 | 0 | 0 |
| 4852 | 12B | 0 | 0 | 0 | 0 | 2 | C0 | 0 | 0 |
| 4842 | 13A | 0 | 0 | 0 | 0 | 0 | R0 | 0 | 0 |
| 4845 | 13B | 0 | 0 | 0 | 0 | 0 | C4 | 1 | 0 |
| 4726 | 8A | 0 | 0 | 0 | 0 | 0 | C4 | 1 | 0 |
| 4727 | 8B | 0 | 0 | 0 | 0 | 0 | C2 | 0 | 0 |
| 4758 | 11B | 0 | 0 | 0 | 0 | 0 | C1 | 0 | 0 |
| 4759 | 11A | 0 | 0 | 0 | 0 | 0 | C4 | 0 | 0 |

NT: not tested
RWW: ml

What is claimed is:

1. A compound having the formula:

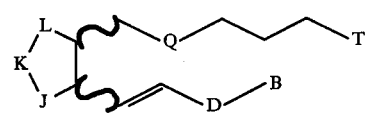

III wherein:
D is a R-hydroxymethylene or S-hydroxymethylene radical;
J is a R-hydroxymethylene or a S-hydroxymethylene radical;
K is a methylene radical;
L is a carbonyl radical;
Q is an ethylene radical;
T is an hydroxymethyl radical; and
B is a monospiroalkyl radical of the formula

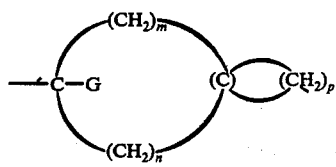

where *m* is an integer having a value of from 0 to 2; *n* is an integer having a value of from 1 to 4; *p* is an integer having a value of from 3 to 11; and the sum of the integers *m* and *n* is less than or equal to 4, and wherein G is hydrogen or lower alkyl of 1 to 3 carbon atoms.

2. A compound according to claim 1 wherein the formula is

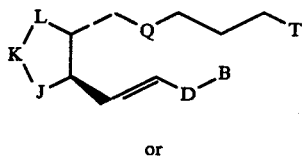

or

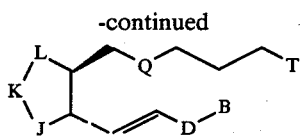

and D, J, K, L, Q, T and B are as defined in claim 1.

3. A compound according to claim 1 wherein *m* is an integer having a value of 1 or 2, *n* is an integer having a value of 1 or 2; and *p* is an integer having a value of from 3 to 5.

4. A compound according to claim 1, wherein the compound is 7-{3R-hydroxy-5-oxo-2R-[3S-hydroxy-3-(spiro[3.3]hept-2-yl)-1E-propenyl]cyclopent-1R-yl}heptan-1-ol.

5. A compound according to claim 1, wherein the compound is 7-{3R-hydroxy-5-oxo-2R-[3R-hydroxy-3-(spiro[3.3]hept-2-yl)-1E-propenyl]cyclopent-1R-yl}heptan-1-ol.

6. A compound according to claim 1, wherein the compound is 7-{3R-hydroxy-5-oxo-2R-[3S-hydroxy-3-(2-methylspiro[3.3]hept-2-yl)-1E-propenyl]cyclopent-1R-yl}heptan-1-ol.

7. A compound according to claim 1, wherein the compound is 7-{3R-hydroxy-5-oxo-2R-[3R-hydroxy-3-(2-methylspiro[3.3]hept-2-yl)-1E-propenyl]cyclopent-1R-yl}heptan-1-ol.

* * * * *